United States Patent
Wu et al.

(10) Patent No.: US 8,470,604 B2
(45) Date of Patent: *Jun. 25, 2013

(54) TRANSIENT DECAY AMPEROMETRY

(75) Inventors: Huan-Ping Wu, Granger, IN (US);
Steven C. Charlton, Osceola, IN (US);
Amy H. Chu, Elkhart, IN (US); Andrew J. Edelbrock, Granger, IN (US);
Sung-Kwon Jung, Granger, IN (US);
Dijia Huang, Granger, IN (US)

(73) Assignee: Bayer HealthCare LLC, Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/210,738

(22) Filed: Aug. 16, 2011

(65) Prior Publication Data
US 2012/0031776 A1    Feb. 9, 2012

Related U.S. Application Data

(63) Continuation of application No. 11/875,942, filed on Oct. 21, 2007, now Pat. No. 8,026,104.

(60) Provisional application No. 60/869,625, filed on Dec. 12, 2006, provisional application No. 60/869,557, filed on Dec. 11, 2006, provisional application No. 60/854,060, filed on Oct. 24, 2006.

(51) Int. Cl.
*G01N 27/333*    (2006.01)
*G01N 33/66*    (2006.01)

(52) U.S. Cl.
USPC ........... 436/149; 205/775; 205/776; 205/777; 205/778; 205/782; 204/403.01

(58) Field of Classification Search
USPC ....... 436/149; 205/775–778, 782; 204/403.01
See application file for complete search history.

(56) References Cited

U.S. PATENT DOCUMENTS
3,420,205 A    1/1969    Morrison
3,505,136 A    4/1970    Attwood
(Continued)

FOREIGN PATENT DOCUMENTS
AU    199920892    12/1998
CA    2423837    10/2000
(Continued)

OTHER PUBLICATIONS

Bayer Healthcare LLC, "Ascensia Autodisc Blood Glucose Test Strips Insert", 2003, Published in: United States.

(Continued)

*Primary Examiner* — Krishnan S Menon
*Assistant Examiner* — Rebecca M Fritchman
(74) *Attorney, Agent, or Firm* — Blanchard & Associates

(57) ABSTRACT

A biosensor system determines an analyte concentration of a biological sample using an electrochemical process without Cottrell decay. The biosensor system generates an output signal having a transient decay, where the output signal is not inversely proportional to the square root of the time. The transient decay is greater or less than the −0.5 decay constant of a Cottrell decay. The transient decay may result from a relatively short incubation period, relatively small sample reservoir volumes, relatively small distances between electrode surfaces and the lid of the sensor strip, and/or relatively short excitations in relation to the average initial thickness of the reagent layer. The biosensor system determines the analyte concentration from the output signal having a transient decay.

50 Claims, 11 Drawing Sheets

U.S. PATENT DOCUMENTS

| | | |
|---|---|---|
| 3,510,268 A | 5/1970 | Hach |
| 3,562,041 A | 2/1971 | Robertson |
| 3,573,139 A | 3/1971 | Eiji Mori et al. |
| 3,690,836 A | 9/1972 | Buissiere et al. |
| 3,715,192 A | 2/1973 | Wenz et al. |
| 3,791,933 A | 2/1974 | Moyer et al. |
| 3,917,453 A | 11/1975 | Milligan et al. |
| 3,937,615 A | 2/1976 | Clack et al. |
| 4,008,448 A | 2/1977 | Muggli |
| 4,053,381 A | 10/1977 | Hamblen et al. |
| 4,077,861 A | 3/1978 | Lauer |
| 4,137,495 A | 1/1979 | Brown |
| 4,225,410 A | 9/1980 | Pace et al. |
| 4,233,029 A | 11/1980 | Columbus |
| 4,260,680 A | 4/1981 | Muramatsu et al. |
| 4,297,184 A | 10/1981 | Dyer |
| 4,303,887 A | 12/1981 | Hill et al. |
| 4,323,536 A | 4/1982 | Columbus |
| 4,366,033 A | 12/1982 | Richter et al. |
| 4,376,689 A | 3/1983 | Nakamura et al. |
| 4,381,775 A | 5/1983 | Nose et al. |
| 4,396,464 A | 8/1983 | Giner et al. |
| 4,402,940 A | 9/1983 | Nose et al. |
| 4,403,984 A | 9/1983 | Ash et al. |
| 4,413,407 A | 11/1983 | Columbus |
| 4,431,004 A | 2/1984 | Bessman et al. |
| 4,473,457 A | 9/1984 | Columbus |
| 4,477,314 A | 10/1984 | Richter et al. |
| 4,490,216 A | 12/1984 | McConnell |
| 4,502,938 A | 3/1985 | Covington et al. |
| 4,561,944 A | 12/1985 | Sasaki et al. |
| 4,571,292 A | 2/1986 | Liu et al. |
| 4,582,684 A | 4/1986 | Vogel et al. |
| 4,591,550 A | 5/1986 | Hafeman et al. |
| 4,654,197 A | 3/1987 | Lilja et al. |
| 4,680,268 A | 7/1987 | Clark |
| 4,686,479 A | 8/1987 | Young et al. |
| 4,714,874 A | 12/1987 | Morris et al. |
| 4,721,677 A | 1/1988 | Clark |
| 4,745,076 A | 5/1988 | Muller et al. |
| 4,746,607 A | 5/1988 | Mura et al. |
| 4,830,959 A | 5/1989 | McNeil et al. |
| 4,854,153 A | 8/1989 | Miyagawa et al. |
| 4,894,137 A | 1/1990 | Takizawa et al. |
| 4,897,162 A | 1/1990 | Lewandowski et al. |
| 4,919,770 A | 4/1990 | Preidel et al. |
| 4,929,330 A | 5/1990 | Osaka et al. |
| 4,929,545 A | 5/1990 | Freitage |
| 4,935,105 A | 6/1990 | Churchouse |
| 4,999,582 A | 3/1991 | Parks et al. |
| 5,046,618 A | 9/1991 | Wood |
| 5,057,447 A | 10/1991 | Paterson |
| 5,108,564 A | 4/1992 | Szuminsky et al. |
| 5,108,819 A | 4/1992 | Heller et al. |
| 5,112,455 A | 5/1992 | Cozzette et al. |
| 5,120,420 A | 6/1992 | Nankai et al. |
| 5,120,421 A | 6/1992 | Glass et al. |
| 5,122,244 A | 6/1992 | Hoenes et al. |
| 5,128,015 A | 7/1992 | Szuminsky et al. |
| 5,140,176 A | 8/1992 | Okino |
| 5,141,868 A | 8/1992 | Shanks et al. |
| 5,217,594 A | 6/1993 | Henkens et al. |
| 5,223,117 A | 6/1993 | Wrighton et al. |
| 5,229,282 A | 7/1993 | Yoshioka et al. |
| 5,243,516 A | 9/1993 | White |
| 5,262,035 A | 11/1993 | Gregg et al. |
| 5,264,103 A | 11/1993 | Yoshioka et al. |
| 5,266,179 A | 11/1993 | Nankai et al. |
| 5,282,950 A | 2/1994 | Dietze et al. |
| 5,286,362 A | 2/1994 | Hoenes et al. |
| 5,288,387 A | 2/1994 | Ito et al. |
| 5,288,636 A | 2/1994 | Pollmann et al. |
| 5,312,590 A | 5/1994 | Gunasingham |
| 5,320,732 A | 6/1994 | Nankai et al. |
| 5,334,296 A | 8/1994 | Henkens et al. |
| 5,352,351 A | 10/1994 | White et al. |
| 5,368,707 A | 11/1994 | Henkens et al. |
| 5,384,028 A | 1/1995 | Ito |
| 5,385,846 A | 1/1995 | Kuhn et al. |
| 5,391,272 A | 2/1995 | O'Daly et al. |
| 5,393,615 A | 2/1995 | Corey et al. |
| 5,393,903 A | 2/1995 | Gratzel et al. |
| 5,405,511 A | 4/1995 | White et al. |
| 5,410,059 A | 4/1995 | Fraser et al. |
| 5,410,474 A | 4/1995 | Fox |
| 5,429,735 A | 7/1995 | Johnson et al. |
| 5,437,999 A | 8/1995 | Diebold et al. |
| 5,438,271 A | 8/1995 | White et al. |
| 5,468,366 A | 11/1995 | Wegner et al. |
| 5,498,542 A | 3/1996 | Corey et al. |
| 5,502,396 A | 3/1996 | Desarzens et al. |
| 5,508,171 A | 4/1996 | Walling et al. |
| 5,509,410 A | 4/1996 | Hill et al. |
| 5,512,159 A | 4/1996 | Yoshioka et al. |
| 5,520,786 A | 5/1996 | Bloczynski et al. |
| 5,554,269 A | 9/1996 | Joseph et al. |
| 5,575,403 A | 11/1996 | Charlton et al. |
| 5,589,045 A | 12/1996 | Hyodo |
| 5,589,326 A | 12/1996 | Deng et al. |
| 5,603,820 A | 2/1997 | Malinski et al. |
| 5,620,579 A | 4/1997 | Genshaw et al. |
| 5,620,890 A | 4/1997 | Kamps-Holtzapple et al. |
| 5,630,986 A | 5/1997 | Charlton et al. |
| 5,644,501 A | 7/1997 | Lin et al. |
| 5,650,062 A | 7/1997 | Ikeda et al. |
| 5,653,863 A | 8/1997 | Genshaw et al. |
| 5,660,791 A | 8/1997 | Brenneman et al. |
| 5,708,247 A | 1/1998 | McAleer et al. |
| 5,710,011 A | 1/1998 | Forrow et al. |
| 5,727,548 A | 3/1998 | Hill et al. |
| 5,755,954 A | 5/1998 | Ludwig et al. |
| 5,759,364 A | 6/1998 | Charlton et al. |
| 5,762,770 A | 6/1998 | Pritchard et al. |
| 5,792,668 A | 8/1998 | Fuller et al. |
| 5,798,031 A | 8/1998 | Charlton et al. |
| 5,807,375 A | 9/1998 | Gross et al. |
| 5,863,400 A | 1/1999 | Drummond et al. |
| 5,865,972 A | 2/1999 | Buffle et al. |
| 5,873,990 A | 2/1999 | Wojciechowski et al. |
| 5,874,046 A | 2/1999 | Megerle et al. |
| RE36,268 E | 8/1999 | Szuminsky et al. |
| 5,942,102 A * | 8/1999 | Hodges et al. ................ 205/775 |
| 5,958,199 A | 9/1999 | Miyamoto et al. |
| 6,004,441 A | 12/1999 | Fujiwara et al. |
| 6,033,866 A | 3/2000 | Guo et al. |
| 6,054,039 A | 4/2000 | Shieh |
| 6,071,391 A | 6/2000 | Gotoh et al. |
| 6,090,268 A | 7/2000 | Akita et al. |
| 6,103,033 A | 8/2000 | Say et al. |
| 6,110,354 A | 8/2000 | Saban et al. |
| 6,120,676 A | 9/2000 | Heller et al. |
| 6,143,164 A | 11/2000 | Heller et al. |
| 6,153,069 A * | 11/2000 | Pottgen et al. ........... 204/403.11 |
| RE36,991 E | 12/2000 | Yamamoto et al. |
| 6,156,173 A | 12/2000 | Gotoh et al. |
| 6,156,673 A | 12/2000 | Hintermaier et al. |
| 6,175,752 B1 | 1/2001 | Say et al. |
| 6,179,979 B1 | 1/2001 | Hodges et al. |
| 6,207,000 B1 | 3/2001 | Schwobel et al. |
| 6,233,471 B1 | 5/2001 | Berner et al. |
| 6,251,260 B1 | 6/2001 | Heller et al. |
| 6,270,637 B1 | 8/2001 | Crismore et al. |
| 6,275,717 B1 | 8/2001 | Gross et al. |
| 6,284,125 B1 | 9/2001 | Hodges et al. |
| 6,294,787 B1 | 9/2001 | Schieferdecker et al. |
| 6,299,757 B1 | 10/2001 | Feldman et al. |
| 6,338,790 B1 | 1/2002 | Feldman et al. |
| 6,344,133 B1 | 2/2002 | Formica et al. |
| 6,391,645 B1 | 5/2002 | Huang et al. |
| 6,413,411 B1 | 7/2002 | Pottgen et al. |
| 6,461,496 B1 | 10/2002 | Feldman et al. |
| 6,475,372 B1 | 11/2002 | Ohara et al. |
| 6,484,046 B1 | 11/2002 | Say et al. |
| 6,503,381 B1 | 1/2003 | Gotoh et al. |
| 6,531,040 B2 | 3/2003 | Musho et al. |
| 6,537,498 B1 | 3/2003 | Lewis et al. |
| 6,551,494 B1 | 4/2003 | Feldman et al. |

| | | |
|---|---|---|
| 6,558,529 B1 | 5/2003 | McVey et al. |
| 6,560,471 B1 | 5/2003 | Heller et al. |
| 6,565,509 B1 | 5/2003 | Say et al. |
| 6,576,101 B1 | 6/2003 | Heller et al. |
| 6,576,117 B1 | 6/2003 | Iketaki et al. |
| 6,591,125 B1 | 7/2003 | Buse et al. |
| 6,592,745 B1 | 7/2003 | Feldmen et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,934 B1 | 9/2003 | Feldmen et al. |
| 6,645,368 B1 | 11/2003 | Beaty et al. |
| 6,676,816 B2 | 1/2004 | Mao et al. |
| 6,689,265 B2 | 2/2004 | Heller et al. |
| 6,699,384 B1 | 3/2004 | Lin et al. |
| 6,749,740 B2 | 6/2004 | Liamos et al. |
| 6,790,341 B1 | 9/2004 | Saba et al. |
| 6,824,669 B1 | 11/2004 | Choong et al. |
| 6,824,670 B2 | 11/2004 | Tokunaga et al. |
| 6,841,052 B2 | 1/2005 | Musho et al. |
| 6,893,545 B2 | 5/2005 | Gotoh et al. |
| 6,942,518 B2 | 9/2005 | Liamos et al. |
| 7,122,111 B2 | 10/2006 | Tokunaga et al. |
| 7,132,041 B2 | 11/2006 | Deng et al. |
| 7,276,146 B2 | 10/2007 | Wilsey |
| 7,276,147 B2 | 10/2007 | Wilsey |
| 7,351,323 B2 | 4/2008 | Iketaki et al. |
| 8,105,478 B2 | 1/2012 | Barlag et al. |
| 2001/0017269 A1 | 8/2001 | Heller et al. |
| 2002/0004106 A1 | 1/2002 | Leddy et al. |
| 2002/0012821 A1 | 1/2002 | Leddy et al. |
| 2002/0053523 A1 | 5/2002 | Liamos et al. |
| 2002/0079219 A1 | 6/2002 | Zhao et al. |
| 2002/0081588 A1 | 6/2002 | De Lumley-woodyear et al. |
| 2002/0084196 A1 | 7/2002 | Liamos et al. |
| 2002/0125146 A1 | 9/2002 | Chan et al. |
| 2002/0157967 A1 | 10/2002 | Ling et al. |
| 2002/0180446 A1 | 12/2002 | Kuhr et al. |
| 2003/0064525 A1 | 4/2003 | Liess |
| 2003/0113933 A1 | 6/2003 | Jansson et al. |
| 2003/0119208 A1 | 6/2003 | Jun et al. |
| 2003/0136673 A1 | 7/2003 | Farruggia et al. |
| 2003/0148169 A1 | 8/2003 | Willner et al. |
| 2003/0159927 A1 | 8/2003 | Lewis et al. |
| 2003/0159944 A1 | 8/2003 | Pottgen et al. |
| 2003/0175737 A1 | 9/2003 | Schulien et al. |
| 2003/0176183 A1 | 9/2003 | Drucker et al. |
| 2003/0178322 A1 | 9/2003 | Bolon et al. |
| 2003/0199744 A1 | 10/2003 | Buse et al. |
| 2003/0201194 A1 | 10/2003 | Heller et al. |
| 2003/0205465 A1 | 11/2003 | Feng et al. |
| 2003/0209450 A1 | 11/2003 | McVey et al. |
| 2004/0005716 A9 | 1/2004 | Beaty et al. |
| 2004/0026253 A1 | 2/2004 | Leddy et al. |
| 2004/0033165 A1 | 2/2004 | Lewis et al. |
| 2004/0040840 A1 | 3/2004 | Mao et al. |
| 2004/0054267 A1 | 3/2004 | Feldmen et al. |
| 2004/0055898 A1 | 3/2004 | Heller et al. |
| 2004/0060818 A1 | 4/2004 | Feldmen et al. |
| 2004/0074772 A1 | 4/2004 | Kumar et al. |
| 2004/0079653 A1 | 4/2004 | Karinka et al. |
| 2004/0099531 A1 | 5/2004 | Srinivasan et al. |
| 2004/0118682 A1 | 6/2004 | Murray et al. |
| 2004/0149577 A1 | 8/2004 | Kumar et al. |
| 2004/0157337 A1 | 8/2004 | Burke et al. |
| 2004/0157338 A1 | 8/2004 | Burke et al. |
| 2004/0157339 A1 | 8/2004 | Burke et al. |
| 2004/0224137 A1 | 11/2004 | Rogalska et al. |
| 2004/0225230 A1 | 11/2004 | Liamos et al. |
| 2004/0259180 A1 | 12/2004 | Burke et al. |
| 2004/0260511 A1 | 12/2004 | Burke et al. |
| 2005/0009126 A1 | 1/2005 | Andrews et al. |
| 2005/0069892 A1 | 3/2005 | Lyengar et al. |
| 2005/0109637 A1 | 5/2005 | Iyengar et al. |
| 2005/0164322 A1 | 7/2005 | Heller et al. |
| 2005/0176153 A1 | 8/2005 | O'hara et al. |
| 2007/0246357 A1 | 10/2007 | Wu |

FOREIGN PATENT DOCUMENTS

| | | |
|---|---|---|
| CA | 2358993 | 5/2001 |
| CN | 1322299 | 10/2000 |
| CN | 1328156 | 12/2001 |
| CN | 1598564 | 10/2004 |
| DE | 229500 | 6/1985 |
| DE | 271179 | 8/1989 |
| DE | 4003194 | 8/1991 |
| DE | 4100727 | 7/1992 |
| DE | 4318891 | 12/1994 |
| DE | 19944318891 | 12/1994 |
| DE | 19824629 | 12/1999 |
| DE | 69915850 | 1/2005 |
| EP | 0120715 | 10/1984 |
| EP | 0121385 | 10/1984 |
| EP | 0127958 | 12/1984 |
| EP | 010375 | 12/1985 |
| EP | 0215678 | 3/1987 |
| EP | 0330517 | 2/1989 |
| EP | 0354441 | 2/1990 |
| EP | 0359831 | 3/1990 |
| EP | 0537761 | 4/1993 |
| EP | 0546796 | 6/1993 |
| EP | 0628810 | 12/1994 |
| EP | 0732590 | 9/1996 |
| EP | 0741186 | 11/1996 |
| EP | 0958495 | 8/1998 |
| EP | 0878708 | 11/1998 |
| EP | 1042667 | 7/1999 |
| EP | 1119637 | 8/2001 |
| EP | 1279742 | 1/2003 |
| EP | 1411348 | 4/2004 |
| EP | 1426757 | 6/2004 |
| EP | 1593958 | 11/2005 |
| ES | 2184236 | 1/2003 |
| ES | 2223185 | 2/2005 |
| FR | 2325920 | 9/1976 |
| JP | 62209350 | 9/1987 |
| JP | 3260739 | 11/1991 |
| JP | 09089832 | 4/1997 |
| JP | 11087213 | 3/1999 |
| JP | 02120657 | 5/1999 |
| JP | 028826 | 1/2003 |
| JP | 061650 | 3/2003 |
| JP | 200403478 | 1/2004 |
| JP | 2004093478 | 3/2004 |
| JP | 2004300328 | 10/2004 |
| JP | 2005147990 | 6/2005 |
| WO | 8203729 | 10/1982 |
| WO | 8600138 | 1/1986 |

OTHER PUBLICATIONS

Parkes, et al., "Balancing Test Time with accurancy and Percision in blood glucose monitoring How fast is too fast?", Jun. 2003.

EPO, "Search Report and Written Opinion for PCT/US2007/081368", May 8, 2008, Publisher: International Searching Authority.

Bard, et al., "Electrochemical Methods Fundamentals and Applications", 1980, p. 236.

Bayer Healthcare LLC, "Glucometer Dex Diabetes Care System; Blood Glucose Test Sensor Disc", 1997, Published in: United States.

Bayer Healthcare LLC, "Glucometer Dex Diabetes Care System; Blood Glucose Test Sensor Cartridge", 2001, Published in: United States.

A.D. Smith, Ed., "Oxford Dictionary of Biochemistry and Molecular Biology, Revised Edition", 2000, pp. 161,476,477,560, Publisher: Oxford University Press.

Yao, et al., "The Low-Potenetail Approach of Glucose Sensing", 1986, pp. 139-146, vol. BME-33, No. 2.

Yao, et al., "A Thin-Film Glucose Electrode System with Compensation for Drifit", 1989, pp. 742-744, vol. XXXV.

Dalrymple, et al., "Peak Shapes in Semidifferential Electroanalysis", Aug. 9, 1977, pp. 1390-1394, vol. 49, No. 9.

* cited by examiner

TRANSIENT DECAY AMPEROMETRY

REFERENCE TO RELATED APPLICATIONS

This application is a continuation of U.S. Nonprovisional application Ser. No. 11/875,942, filed Oct. 21, 2007, entitled "Transient Decay Amperometry," which claims the benefit of U.S. Provisional Application No. 60/854,060 entitled "Transient Decay Amperometry" filed Oct. 24, 2006, which is incorporated by reference in its entirety, the benefit of U.S. Provisional Application No. 60/869,557 entitled "Transient Decay Amperometry" filed Dec. 11, 2006, which is incorporated by reference in its entirety, and the benefit of U.S. Provisional Application No. 60/869,625 entitled "Transient Decay Amperometry" filed Dec. 12, 2006, which is incorporated by reference in its entirety.

BACKGROUND

Biosensors provide an analysis of a biological fluid, such as whole blood, urine, or saliva. Typically, a biosensor analyzes a sample of the biological fluid to determine the concentration of one or more analytes, such as alcohol, glucose, uric acid, lactate, cholesterol, or bilirubin, in the biological fluid. The analysis is useful in the diagnosis and treatment of physiological abnormalities. For example, a diabetic individual may use a biosensor to determine the glucose level in whole blood for adjustments to diet and/or medication.

Biosensors may be implemented using bench-top, portable, and like measurement devices. The portable measurement devices may be hand-held. Biosensors may be designed to analyze one or more analytes and may use different volumes of biological fluids. Some biosensors may analyze a single drop of whole blood, such as from 0.25-15 microliters ($\mu L$) in volume. Examples of portable measurement devices include the Ascensia Breeze® and Elite® meters of Bayer Corporation; the Precision® biosensors available from Abbott in Abbott Park, Ill.; Accucheck® biosensors available from Roche in Indianapolis, Ind.; and OneTouch Ultra® biosensors available from Lifescan in Milpitas, Calif. Examples of bench-top measurement devices include the BAS 100B Analyzer available from BAS Instruments in West Lafayette, Ind.; the Electrochemical Workstation available from CH Instruments in Austin, Tex.; another Electrochemical Workstation available from Cypress Systems in Lawrence, Kans.; and the EG&G Electrochemical Instrument available from Princeton Research Instruments in Princeton, N.J.

Biosensors usually measure an electrical signal to determine the analyte concentration in a sample of the biological fluid. The analyte typically undergoes an oxidation/reduction or redox reaction when an input signal is applied to the sample. An enzyme or similar species may be added to the sample to enhance the redox reaction. The input signal usually is an electrical signal, such as a current or potential. The redox reaction generates an output signal in response to the input signal. The output signal usually is an electrical signal, such as a current or potential, which may be measured and correlated with the concentration of the analyte in the biological fluid.

Many biosensors include a measurement device and a sensor strip. The sensor strip may be adapted for use outside, inside, or partially inside a living organism. When used outside a living organism, a sample of the biological fluid is introduced into a sample reservoir in the sensor strip. The sensor strip may be placed in the measurement device before, after, or during the introduction of the sample for analysis. When inside or partially inside a living organism, the sensor strip may be continually immersed in the sample or the sample may be intermittently introduced to the strip. The sensor strip may include a reservoir that partially isolates a volume of the sample or be open to the sample. Similarly, the sample may continuously flow through the strip or be interrupted for analysis.

The measurement device usually has electrical contacts that connect with the electrical conductors of the sensor strip. The electrical conductors typically connect to working, counter, and/or other electrodes that extend into the sample reservoir. The measurement device applies the input signal through the electrical contacts to the electrical conductors of the sensor strip. The electrical conductors convey the input signal through the electrodes into the sample present in the sample reservoir. The redox reaction of the analyte generates an output signal in response to the input signal. The measurement device determines the analyte concentration in response to the output signal.

The sensor strip may include reagents that react with the analyte in the sample of biological fluid. The reagents may include an ionizing agent to facilitate the redox reaction of the analyte, as well as mediators or other substances that assist in transferring electrons between the analyte and the conductor. The ionizing agent may be an oxidoreductase, such as an analyte specific enzyme, which catalyzes the oxidation of glucose in a whole blood sample. The reagents may include a binder that holds the enzyme and mediator together.

Many biosensors use amperometric methods where an electrical signal of constant potential (voltage) is applied to the electrical conductors of the sensor strip while the measured output signal is a current. Thus, in an amperometric system current may be measured as a constant potential is applied across the working and counter electrodes of the sensor strip. The measured current then may be used to determine the presence of and/or quantify the analyte in the sample. Amperometry measures the rate at which the measurable species, and thus the analyte, is being oxidized or reduced at the working electrode. In addition to analytes, biological substrates and mediators, for example, may serve as measurable species As the time during which the input signal is applied to the sensor strip increases, the rate at which the measurable species is oxidized or reduced at the working electrode decreases. Thus, after an initial period of high current output, the current recorded from the sensor strip decreases as the input signal continues to be applied. This current decrease with time may be referred to as an electrochemical decay, and the rate of this decay may be correlated with the concentration of measurable species, and thus the analyte, in the sample. An electrochemical decay may be a transient or Cottrell decay.

The electrochemical decay may be correlated with the analyte concentration in the sample by expressing the decay with an equation describing a line that relates current with time by the natural log function (In), for example. Thus, the output current may be expressed as a function of time with an exponential coefficient, where negative exponential coefficients indicate a decay process. After the initial decrease in current output, the rate of decrease may remain relatively constant or continue to fluctuate.

U.S. Pat. No. 5,942,102 ("the '102 patent") describes the relationship between measured output current and time during a conventional analysis. An electrical signal is input to a sensor strip about 60 seconds after introduction of the whole blood sample to the strip. Initially, a rapidly decreasing current is observed, which is followed by a relatively constant or "steady-state" current output that is generated by the feedback of mediator from the counter to the working electrode.

The feedback of the mediator provided by the short distance between the electrodes results in the current becoming substantially independent of time after the initial decrease. In this conventional analysis, the analyte concentration of the sample may be determined from the concentration and diffusion coefficient of the mediator as determined by: (1) measuring current as a function of time; and then (2) estimating the steady state current.

While the analysis method described in the '102 patent relies on the steady-state portion of the current decay, U.S. Pat. Nos. 6,153,069 ("the '069 patent") and 6,413,411 ("the '411 patent") describe methods where the concentration of a mediator, and thus the underlying analyte, is determined from the diffusion coefficient of the mediator. These systems are configured to provide a rate of current decay that is described by the Cottrell equation.

Current measurements demonstrate Cottrell decay when the measured current is inversely proportional to the square root of time. Current measurements with Cottrell decay may be described by the Cottrell equation given below as Equation (1):

$$i(t) = nFAC^b \left(\frac{D}{\pi t}\right)^{1/2} = nFAC^b \left(\frac{D}{\pi}\right)^{1/2} t^{-0.5}, \quad (1)$$

where i is the measured current; $C^b$ is the bulk concentration of the electrochemically active species in mol/cm$^3$; A is the electrode area in cm$^2$; F is the Faraday constant of 96,500 coul/equivalent; n is the number of electrons transferred in equivalents/mol.; D is the diffusion coefficient in cm$^2$/sec; and t is the time of the electrochemical reaction in seconds. Thus, the Cottrell equation describes current as an exponential function of time, having a decay constant or exponential coefficient of –0.5. Further details of the Cottrell equation and the boundary conditions required for Cottrell behavior may be found in chapter 5, pp. 136-45, of Electrochemical Methods: Fundamentals and Applications by Bard and Faulkner (1980).

A system designed to operate with a Cottrell current decay requires a decay constant of –0.5. An electrochemical system demonstrating a –0.5 decay constant implies that the requirements of a Cottrell current are present, namely that the analyte has completely converted to a measurable species and that a substantially constant concentration distribution of this measurable species occupies the sample reservoir before current measurement. These requirements are further described in the '069 and '411 patents.

Column 4, Lines 39-40 of the '411 patent discloses that initial incubation periods of 15 to 90 seconds, preferably from 20 to 45 seconds, are used for glucose testing. After the initial incubation period and application of a single excitation input signal, current measurements demonstrating Cottrell decay may be recorded from 2 to 30 seconds or preferably from 10 to 20 seconds following application of the input signal to the sensor strip. The requirement of a longer initial incubation period also is depicted in FIG. 7 of the '411 patent, where the sample was allowed to react in the sensor strip (incubate) for 160 seconds before application of the input signal.

The longer incubation periods required to completely convert the analyte to measurable species provide: (1) time for hydration of the reagent layer containing the reagents; and (2) time for the reagents to convert the analyte. For example, column 4, lines 36-44 of the '411 patent describes an incubation period of sufficient length to allow the enzymatic reaction to reach completion. After this incubation period, where the glucose analyte is fully converted to a measurable species, the instrument imposes a known potential across the electrodes to measure the resulting diffusion limited (i.e. Cottrell) current at specific times during the resulting Cottrell current decay. Thus, the conversion of the analyte to the measurable species is completed before Cottrell decay is observed. Complete hydration of the reagent layer also is recognized in the '411 patent as a requirement for Cottrell decay. The '411 patent discloses that incomplete wetting of the reagent results in a failure of the system to follow the Cottrell curve decay, which results in an inaccurate analyte concentration value being obtained.

In addition to an extended incubation period, Cottrell decay also requires a substantially constant concentration distribution of a measurable species in the sample as the distance from the electrode surface increases. A substantially constant concentration distribution may be achieved with: (1) relatively large sample volumes; and/or (2) a relatively large distance between facing planar electrodes or substantially planar electrodes and the bottom surface of the sensor strip lid. For example, column 8, line 40 of the '069 patent describes a working electrode occupying a sample reservoir providing a 50 μL sample volume where the vertical distance between the working electrode and the lid is from 500-2000 μm. In another example, unlike the closely spaced electrodes of the '102 patent, the distance between the working and counter electrodes described in column 7, lines 62-66 of the '411 patent must be at least 100 microns, and preferably greater than 100 microns.

Conventional analysis methods typically lengthen the time required to analyze samples by requiring incubation periods, electrode distances, and sample reservoir volumes sufficient to allow the system to have Cottrell decay. Accordingly, there is an ongoing need for improved biosensors; especially those that more quickly determine the analyte concentration of a sample and do not rely on the estimation of a steady state current value. The systems, devices, and methods of the present invention overcome at least one of the disadvantages associated with conventional biosensors.

SUMMARY

The present invention provides a biosensor system that determines an analyte concentration of a biological sample from an output signal having a transient decay. The output signal is not inversely proportional to the square root of the time, and thus has a decay constant greater or less than the decay constant of a Cottrell decay.

In one aspect, a method for determining an analyte concentration in a sample includes applying an input signal to the sample after an incubation period, generating an output signal having a transient decay in response to a redox reaction of a measurable species; and determining the analyte concentration from the output signal. The analyte may glucose and the sample may be introduced to a sensor strip. The method may include transferring at least one electron from or to the analyte in the sample to form the measurable species, which may include at least one mediator.

The input signal may include at least two excitations separated by a relaxation, where the at least two excitations have durations from 0.1 to 5 seconds and the duration of the relaxation is at least 0.1 second or at least 0.5 second. Each excitation and/or relaxation duration may be the same or different. The duration for one or more of the relaxations may be from 0.1 to 3 seconds. The input signal may include at least three excitations and at least two relaxations. The input signal may include at least 2 duty cycles applied within 5 seconds.

The incubation period may be from 0.1 to 8 seconds, from 0.1 to 6 seconds, or from 0.5 to 4.75 seconds, for example. The incubation period and the application of the input signal may be complete in at most 12, at most 6, or at most 4 seconds. The transient decay may have a decay constant from −0.52 to −1, or from −0.001 to −0.48. The transient decay may have a decay constant of at most −0.45 or at most −0.35. The output signal from which the analyte concentration is determined may include a current value recorded within 2 seconds of applying the input signal to the sample. The analyte concentration of the sample may be determined within at most 6, 3, or 1.5 seconds of applying the input signal.

The sample may reside in a reservoir defined by a sensor strip base and the bottom surface of a lid, the base being 20 to 200 micrometers from the bottom surface of the lid. The volume of sample within the reservoir may be from 0.25 to 10 microliters for from 0.25 to 1.5 microliter. The reservoir may include at least one reagent layer having an average initial thickness of at most 20 micrometers, less than 14 micrometers, or at most 5 micrometers. The reservoir may include at least one reagent layer having an average initial thickness of at most 2 micrometers when the input signal includes at least two excitations, at least one of the excitations having a duration of at most 0.5 seconds. The reservoir may include at least one reagent layer comprising a distinct diffusion barrier layer.

The reservoir height from the sensor strip base to the bottom of the lid may be at most 250 micrometers, the volume of the sample within the reservoir may be at most 5 microliters, the reservoir may include at least one reagent layer having an average initial thickness of at most 20 micrometers, and the incubation period may be at most 12 seconds. The reservoir height from the sensor strip base to the bottom of the lid may be at most 150 micrometers, the volume of the sample within the reservoir may be at most 3.5 microliters, the reservoir may include at least one reagent layer having an average initial thickness of less than 14 micrometers, and the incubation period may be at most 6 seconds. The reservoir height from the sensor strip base to the bottom of the lid may be at most 100 micrometers, the volume of the sample within the reservoir may be at most 3 microliters, the reservoir may include at least one reagent layer having an average initial thickness of at most 2 micrometers, and the incubation period may be at most 2 seconds.

In another aspect, a method for determining an analyte concentration in a sample includes applying an input signal to the sample after an incubation period of at most 12 seconds; generating an output signal having a transient decay in response to a redox reaction of a measurable species; and determining the analyte concentration from the output signal.

In another aspect, a biosensor for determining an analyte concentration in a sample includes a measurement device having a processor connected to a sensor interface; a sensor strip having a sample interface on a base, the sensor interface in electrical communication with the sample interface, where the sample interface is adjacent to a reservoir formed by the base; where the processor instructs a charger to apply an input signal to the reservoir after an incubation period of at most 12 seconds; and where the processor determines the analyte concentration in the sample from an output signal having a transient decay in response to a redox reaction of the analyte in the sample.

The reservoir may include at least one working electrode in electrical communication with the charger, a reagent layer on the working electrode having a combination DBL/reagent layer with an average initial thickness from about 1 micrometer to about 20 micrometers. The combination DBL/reagent layer may have an average initial thickness of at most 1 micrometer.

In another aspect, a method for determining an analyte concentration in a sample includes applying an input signal to the sample after an incubation period of at most 12 seconds; generating a variant concentration distribution of a measurable species in a sample reservoir; generating an output signal in response to a redox reaction of a measurable species; and determining the analyte concentration from the output signal.

In another aspect, a method for determining an analyte concentration in a sample includes introducing the sample to a sensor strip; applying an input signal to the sample after an incubation period of at most 8 seconds; generating an output signal having a transient decay in response to a redox reaction of a measurable species; and determining the analyte concentration from the transient decay of the output signal. The transient decay may be a decreasing current decay obtained within 0.5 to 5 seconds or in about 0.5 to about 3 seconds of applying the input signal to the sample.

BRIEF DESCRIPTION OF THE DRAWINGS

The invention can be better understood with reference to the following drawings and description. The components in the figures are not necessarily to scale, emphasis instead being placed upon illustrating the principles of the invention.

DETAILED DESCRIPTION

A biosensor system uses an electrochemical process lacking a Cottrell decay constant to determine an analyte concentration of a biological sample. The biosensor system generates an output signal from the biological sample having a transient decay, where the output signal is not inversely related to the square root of the time. The transient decay output from the biosensor system has a decay constant greater or less than −0.5 and the system does not rely on an estimation of a steady state current value to determine the analyte concentration. Preferably, transient decays from which analyte concentrations are determined continually decrease.

Cottrell decay is diffusion dependent and may not exist unless the analyte has completely converted to a measurable species and a substantially constant concentration distribution of this measurable species occupies the sample reservoir before current measurement. Relatively long incubation times and large sample volumes are required to obtain Cottrell decay. Without these conditions, the output current will not be inversely related to the square root of time and thus biosensors will not exhibit the −0.5 decay constant required for Cottrell decay. Biosensors designed to operate with Cottrell decay will provide inaccurate analyses if the output current is not inversely related to the square root of time or if a decay constant other than −0.5 is present in the output signal.

The present biosensor system operates using transient decays, where decay constants smaller or larger than −0.5 are observed. The transient and thus non-Cottrell decay constants may result from a relatively short incubation period. Transient decay constants also may result from relatively small sample reservoir volumes, relatively small distances between electrode surfaces and the lid of the sensor strip, and/or relatively short excitations in relation to the average initial thickness of the reagent layer.

To generate an output current with a transient decay or transient decay constants greater or less than −0.5, the biosensor system may use incubation periods of 12 seconds or less, reservoir volumes of 5 µL or less, reservoir heights of 200 µm or less, and/or an average initial thickness for the reagent layer of 20 µm or less. Preferable incubation periods for use with reservoir volumes of 3.5 µL or less, reservoir heights of 150 µm or less, and/or an average initial thickness for the reagent layer of 10 µm or less are at most 8 seconds, at most 6 seconds, or at most 4 seconds. At present, especially preferred incubation periods for use with sample strip sample volumes of 3.0 µL or less, sample strip cap-gap heights of 100 µm or less, and/or an average initial thickness for the reagent layer of 2 µm or less are at most 2 seconds or at most 1 second. Other incubation periods, reservoir volumes, reservoir heights, and reagent layer thicknesses may be used.

Figure 1A:
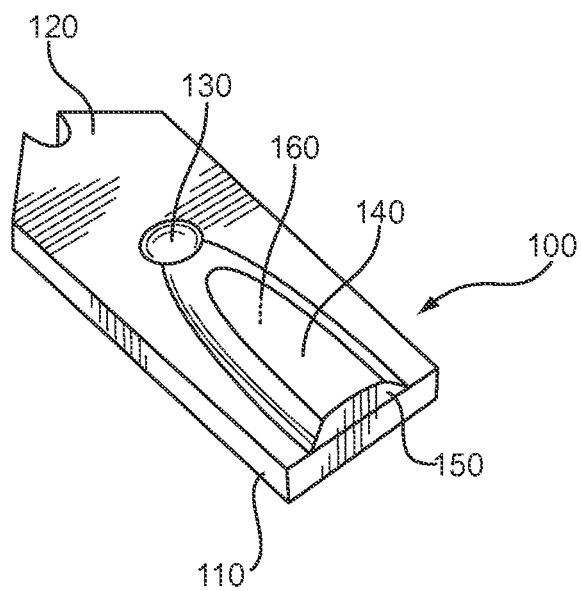
FIG. 1A is a perspective representation of an assembled sensor strip.
Figure 1B:
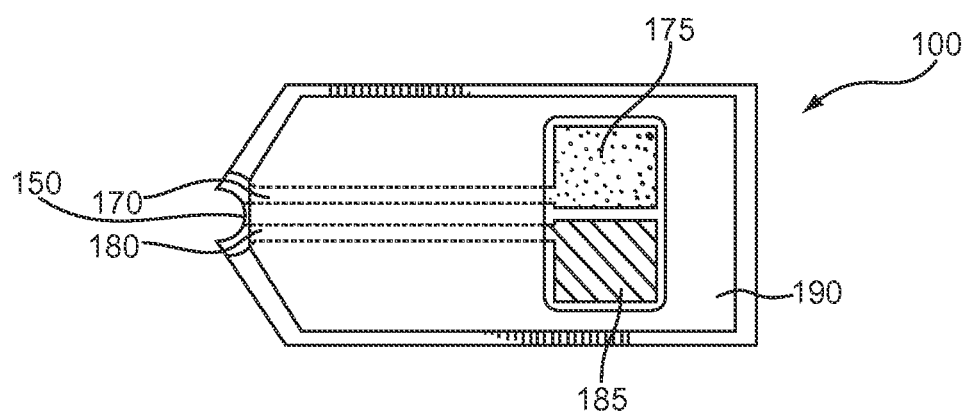
FIG. 1B is a top-view diagram of a sensor strip, with the lid removed.

FIGS. 1A and 1B depict a sensor strip 100, which may be used with the biosensor system. FIG. 1A is a perspective view of an assembled sensor strip 100 including a sensor base 110, at least partially covered by a lid 120 that includes a vent 130, a sample coverage area 140, and an input end opening 150. A partially-enclosed sample reservoir 160 (the capillary gap or cap-gap) is formed between the base 110 and the lid 120. Other sensor strip designs also may be used, such as those described in U.S. Pat. Nos. 5,120,420 and 5,798,031. While a particular configuration is shown in FIGS. 1A-1B, the sensor strip 100 may have other configurations, including those with additional components.

The height of the reservoir 160 between the sensor base 110 and the lid 120 may be from 20 to 250 micrometers (µm), more preferably from 50 to 150 µm. The volume of the reservoir 160 may be from 0.25 to 10 µL, preferably from 0.8 to 4 µL, and more preferably from 0.5 to 1.5 µL. Other heights and volumes may be used.

A liquid sample for analysis may be transferred into the reservoir 160 by introducing the liquid to the opening 150. The liquid fills the reservoir 160 while expelling the previously contained air through the vent 130. The reservoir 160 may contain a composition (not shown) that assists in retaining the liquid sample in the reservoir. Examples of such compositions include: water-swellable polymers, such as carboxymethyl cellulose and polyethylene glycol; and porous polymer matrices, such as dextran and polyacrylamide.

FIG. 1B depicts a top-view of the sensor strip 100, with the lid 120 removed. Conductors 170 and 180 may run under a dielectric layer 190 from the opening 150 to a working electrode 175 and a counter electrode 185, respectively. The sensor strip 100 may include more than one working electrode. The working and counter electrodes 175, 185 may be in substantially the same plane. The electrodes may be in another orientation. The dielectric layer 190 may partially cover the electrodes 175, 185 and may be made from any suitable dielectric material, such as an insulating polymer. While a particular electrode configuration is shown, the electrodes may have other configurations, including those with additional components.

The counter electrode 185 may support the electrochemical activity at the working electrode 175 of the sensor strip 100. The potential to support the electrochemical activity at the working electrode 175 may be provided to the sensor system by forming the counter electrode 185 from an inert material, such as carbon, and including a soluble redox species, such as ferricyanide, within the reservoir 160. The potential at the counter electrode 185 may be a reference potential achieved by forming the counter electrode 185 from a redox pair, such as Ag/AgCl, to provide a combined reference-counter electrode. A redox pair includes two conjugate species of a chemical substance having different oxidation numbers. Reduction of the species having the higher oxidation number produces the species having the lower oxidation number. Alternatively, oxidation of the species having the lower oxidation number produces the species having the higher oxidation number. The sensor strip 100 may be provided with a third conductor and electrode to provide a reference potential to the sensor system.

The working and counter electrodes 175, 185 may be separated by greater than 200 µm or 250 µm. The working and counter electrodes 175, 185 may be separated by less than 200 µm. The working and counter electrodes 175, 185 may be separated by other distances.

Figure 2A:
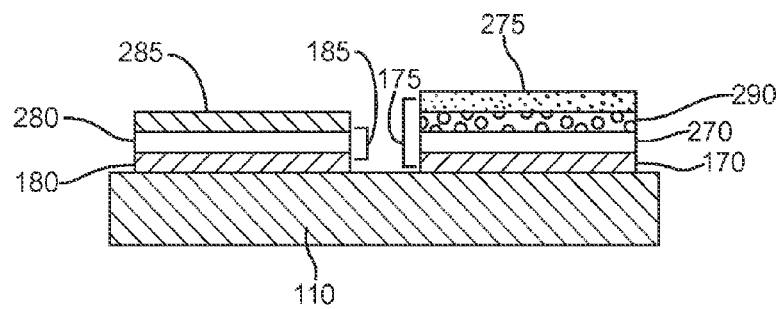
FIG. 2A is an end view diagram of the sensor strip of FIG. 1B.

FIG. 2A depicts an end view of the sensor strip 100 depicted in FIG. 1B, showing the layer structure of the working electrode 175 and the counter electrode 185 residing within the reservoir 160. The conductors 170 and 180 may lie on the base 110. Other materials may reside between the conductors 170, 180 and the base 110, thus the conductors may or may not be in physical contact with the base. A portion of the conductors may penetrate a portion of the base. Surface conductor layers 270 and 280 optionally may be deposited on the conductors 170 and 180, respectively. Other materials may reside between the surface conductor layers 270, 280 and the conductors 170, 180, thus the surface conductors may or may not be in physical contact with the conductors. A portion of the surface conductors may penetrate a portion of the conductors. The surface conductor layers 270, 280 may be made from the same or from different materials.

The material or materials forming the conductors 170, 180 and the surface conductor layers 270, 280 may include any electrical conductor. The conductors 170, 180 preferably include a thin layer of a metal paste or metal, such as gold, silver, platinum, palladium, copper, or tungsten. The surface conductor layers 270, 280 preferably include carbon, gold, platinum, palladium, or combinations thereof. Preferable electrical conductors are non-ionizing, such that the material does not undergo a net oxidation or a net reduction during analysis of the sample. Thus, if a surface conductor layer is not on a conductor, the conductor is preferably made from a non-ionizing material, such as carbon, gold, platinum, palladium, or combinations thereof.

The surface conductor material may be deposited on the conductors 170, 180 by any conventional means compatible with the operation of the sensor strip, including foil deposition, chemical vapor deposition, slurry deposition, and the like. In the case of slurry deposition, the conductor material may be applied as an ink to the conductors 170, 180, as described in U.S. Pat. No. 5,798,031.

The reagent layers 275 and 285 may be deposited on the conductors 170 and 180, respectively. The layers are formed from at least one reagent composition that may include a binder. The binder is preferably a polymeric material that is at least partially water-soluble. The binder may form a gel or gel-like material when hydrated. The binder may form a gel or gel-like material in combination with the reagents when hydrated. The gel or gel-like material may inhibit and/or filter red blood cells from reaching the surface conductor 270 and/or the conductor 170.

Suitable partially water-soluble polymeric materials for use as the binder may include poly(ethylene oxide) (PEO), carboxymethyl cellulose (CMC), polyvinyl alcohol (PVA), hydroxyethyl cellulose (HEC), hydroxypropyl cellulose (HPC), methyl cellulose, ethyl cellulose, ethyl hydroxyethyl cellulose, carboxymethyl ethyl cellulose, polyvinyl pyrrolidone (PVP), polyamino acids, such as polylysine, polystyrene sulfonate, gelatin, acrylic acid, methacrylic acid, starch, maleic anhydride salts thereof, derivatives thereof, and combinations thereof. Among the above binder materials, PEO, PVA, CMC, and HEC are preferred, with CMC being more preferred at present.

In addition to the binder, the reagent layers 275 and 285 may include the same or different reagents. When including the same reagents, the reagent layers 275 and 285 may be the same layer. In one aspect, the reagents present in the first layer 275 may be selected for use with the working electrode 175, while the reagents present in the second layer 285 may be selected for use with the counter electrode 185. For example, the reagents in the layer 285 may facilitate the flow of electrons between the sample and the conductor 180. Similarly, the reagents in the layer 275 may facilitate the reaction of the analyte.

The reagent layer 275 may include an enzyme system specific to the analyte that may enhance the specificity of the sensor system to the analyte, especially in complex biological samples. The enzyme system may include one or more enzyme, cofactor, and/or other moiety that participates in the redox reaction of the analyte. For example, an alcohol oxidase can be used to provide a sensor strip that is sensitive to the presence of alcohol in a sample. Such a system may be useful in measuring blood alcohol concentrations. In another example, glucose dehydrogenase or glucose oxidase may be used to provide a sensor strip that is sensitive to the presence of glucose in a sample. This system may be useful in measuring blood glucose concentrations, for example in patients known or suspected to have diabetes.

Enzymes for use in the enzyme system include alcohol dehydrogenase, lactate dehydrogenase, β-hydroxybutyrate dehydrogenase, glucose-6-phosphate dehydrogenase, glucose dehydrogenase, formaldehyde dehydrogenase, malate dehydrogenase, and 3-hydroxysteroid dehydrogenase. Preferable enzyme systems may be oxygen independent, thus not substantially oxidized by oxygen.

One such oxygen independent enzyme family for use in a glucose sensor strip is glucose dehydrogenase (GDH). Using different co-enzymes or co-factors, GDH may be mediated in a different manner by different mediators. Depending on the association with GDH, a co-factor, such as flavin adenine dinucleotide (FAD), can be tightly held by the host enzyme, such as in the case of FAD-GDH; or a co-factor, such as Pyrroloquinoline quinone (PQQ), may be covalently linked to the host enzyme, such as with PQQ-GDH. The co-factor in each of these enzyme systems may be held by the host enzyme, or the co-enzyme and the apo-enzyme may be re-constituted before the enzyme system is added to the reagent composition. The co-enzyme also may be independently added to the host enzyme in the reagent composition to assist in the catalytic function of the host enzyme, such as in the cases of nicotinamide adenine dinucleotide $NAD/NADH^+$ or nicotinamide adenine dinucleotide phosphate $NADP/NADPH^+$.

The reagent layer 275 also may include a mediator to more effectively communicate the results of the analyte redox reaction to the surface conductor 270 and/or the conductor 170. Mediators may be separated into two groups based on their electrochemical activity. One electron transfer mediators are capable of taking on one additional electron during electrochemical reactions. Examples of one electron transfer mediators include compounds, such as 1,1'-dimethyl ferrocene, ferrocyanide and ferricyanide, and ruthenium(III) hexaamine. Two electron transfer mediators are capable of taking on two additional electrons.

Two electron mediators include the organic quinones and hydroquinones, such as phenanthroline quinone; phenothiazine and phenoxazine derivatives; 3-(phenylamino)-3H-phenoxazines; phenothiazines; and 7-hydroxy-9,9-dimethyl-9H-acridin-2-one and its derivatives. Examples of additional two electron mediators include the electroactive organic molecules described in U.S. Pat. Nos. 5,393,615; 5,498,542; and 5,520,786, which are incorporated herein by reference. Other electroactive organic molecules include organic molecules lacking a metal that are capable of undergoing a redox reaction. Electroactive organic molecules can behave as redox species and/or as mediators. Examples of electro-active organic molecules include coenzyme pyrroloquinoline quinone (PQQ), benzoquinones and naphthoquinones, N-oxides, nitroso compounds, hydroxylamines, oxines, flavins, phenazines, phenothiazines, indophenols, and indamines.

Preferred two electron transfer mediators include 3-phenylimino-3H-phenothiazines (PIPT) and 3-phenylimino-3H-phenoxazines (PIPO). More preferred two electron mediators include the carboxylic acid or salt, such as ammonium salts, of phenothiazine derivatives. At present, especially preferred two electron mediators include (E)-2-(3H-phenothiazine-3-ylideneamino)benzene-1,4-disulfonic acid, (E)-5-(3H-phenothiazine-3-ylideneamino)isophthalic acid, ammonium (E)-3-(3H-phenothiazine-3-ylideneamino)-5-carboxybenzoate, and combinations thereof. Preferred two electron mediators may have a redox potential that is at least 100 mV lower, more preferably at least 150 mV lower, than ferricyanide.

The reagent layers 275, 285 may be deposited by any convenient means, such as printing, liquid deposition, or ink-jet deposition. In one aspect, the layers are deposited by printing. With other factors being equal, the angle of the printing blade may inversely affect the initial thickness of the reagent layer. For example, when the blade is moved at an approximately 82° angle to the base 110, the layer may have an initial thickness of approximately 10 µm. Similarly, when a blade angle of approximately 62° to the base 110 is used, a thicker 30 µm layer may be produced. Thus, lower blade angles may provide thicker reagent layers. In addition to blade angle, other factors, such as the viscosity of the reagent composition as well as the screen-size and emulsion combination, may affect the resulting thickness of the reagent layers 275, 285.

When thinner reagent layers are preferred, deposition methods other than printing, such as micro-pipetting, ink jetting, or pin-deposition, may be used. These deposition methods generally give the dry reagent layers at micrometer or sub-micrometer thickness, such as 1-2 µm. For example, pin-deposition methods may provide an average initial thickness of about 1 µm for the reagent layer. The thickness of the reagent layer resulting from pin-deposition, for example, may be controlled by the amount of polymer included in the reagent composition, with higher polymer content providing thicker reagent layers. Thinner reagent layers may require shorter excitation durations than thicker reagent layers to maintain the desired measurement performance and/or substantially measure analyte within the diffusion barrier layer (DBL).

The working electrode 175 may include a DBL that is integral to a reagent layer 275 or that is a distinct layer 290, such as depicted in FIG. 2A. Thus, the DBL may be formed as a combination reagent/DBL on the conductor, as a distinct layer on the conductor, or as a distinct layer on the reagent layer. When the working electrode 175 includes the distinct DBL 290, the reagent layer 275 may or may not reside on the DBL 290. Instead, the reagent layer 275 may reside on any portion of the sensor strip 100 that allows the reagent to solubilize in the sample. For example, the reagent layer 175 may reside on the base 110 or on the lid 120.

The DBL provides a porous space having an internal volume where a measurable species may reside and also may filter red blood cells from the conductor surface. The pores of the DBL may be selected so that the measurable species may diffuse into the DBL, while physically larger sample constituents, such as red blood cells, are substantially excluded. Although conventional sensor strips have used various materials to filter red blood cells from the surface of the working electrode, a DBL provides an internal porous space to contain and isolate a portion of the measurable species from the sample.

When the reagent layer 275 includes a water-soluble binder, any portion of the binder that does not solubilize into the sample prior to the application of an excitation may function as an integral DBL. The average initial thickness of a combination DBL/reagent layer is preferably less than 20 or 10 µm and more preferably less than 5 µm. The desired average initial thickness of a combination DBL/reagent layer may be selected for a specific excitation length on the basis of when the diffusion rate of the measurable species from the DBL to a conductor surface, such as the surface of the conductor 170 or the surface of the surface conductor 270 from FIG. 2A, becomes relatively constant. The combination DBL/reagent layer may have an average initial thickness of 2 µm, 1 µm, or less when combined with an excitation duration of 0.25 seconds or less.

The distinct DBL 290 may include any material that provides the desired pore space, while being partially or slowly soluble in the sample. The distinct DBL 290 may include a reagent binder material lacking reagents. The distinct DBL 290 may have an average initial thickness from 1 to 15 µm, and more preferably from 2 to 5 µm.

Figure 2B:
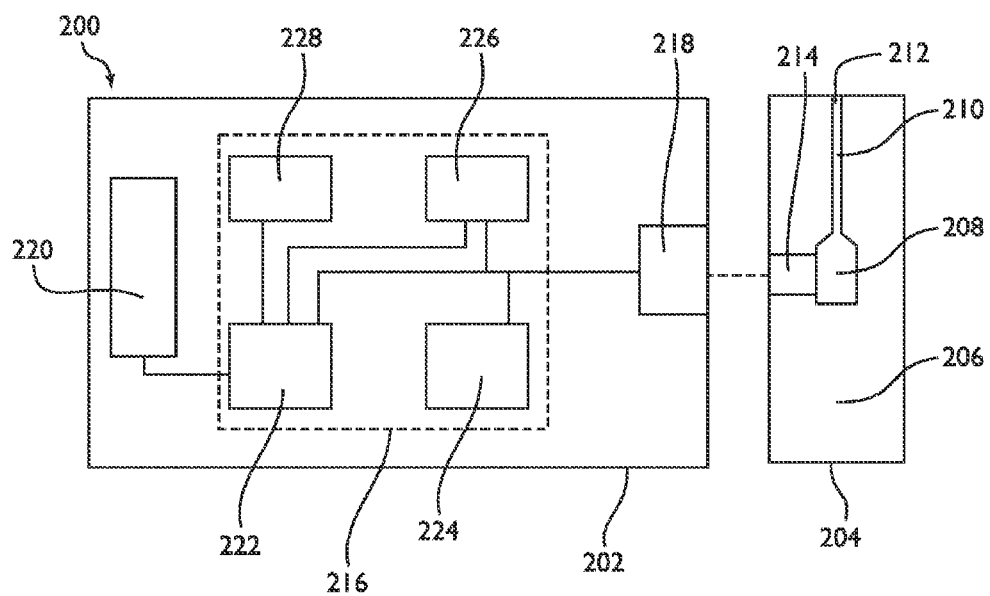
FIG. 2B depicts a schematic representation of a biosensor system that determines an analyte concentration in a sample.

FIG. 2B depicts a schematic representation of a biosensor system 200 that determines an analyte concentration in a sample, such as a biological fluid. The biosensor system 200 includes a measurement device 202 that performs an analysis method and a sensor strip 204. The sensor strip 204 may be an electrochemical sensor strip as depicted in FIGS. 1A, 1B, and 2A, for example. The measurement device 202 may be implemented as a bench-top device, a portable or hand-held device, or the like. The measurement device 202 and the sensor strip 204 may implement an electrochemical analysis, an optical analysis, a combination thereof, or the like. The biosensor system 200 may determine analyte concentrations, including those of alcohol, glucose, uric acid, lactate, cholesterol, bilirubin, and the like in biological samples. While a particular configuration is shown, the biosensor system 200 may have other configurations, including those with additional components.

The sensor strip 204 has a base 206 that forms a sample reservoir 208 and a channel 210 with an opening 212. Referring to FIG. 1A, the channel 210 may be integral to the reservoir 208. The reservoir 208 and the channel 210 may be covered by a lid with a vent. The reservoir 208 defines a partially-enclosed volume (the cap-gap). The reservoir 208 may contain a composition that assists in retaining a liquid sample, such as water-swellable polymers or porous polymer matrices. Reagents may be deposited in the reservoir 208 and/or channel 210. The reagent composition may include one or more enzymes, binders, mediators, and the like. The reagents may include a chemical indicator for an optical system. The sensor strip 204 may have other configurations.

The sensor strip 204 also may have a sample interface 214. In an electrochemical system, the sample interface 214 has conductors connected to at least two electrodes, such as a working electrode and a counter electrode. The electrodes may be disposed on a surface of the base 206 that forms the reservoir 208. The sample interface 214 may have other electrodes and/or conductors.

The measurement device 202 includes electrical circuitry 216 connected to a sensor interface 218 and a display 220. The electrical circuitry 216 may include a processor 222 connected to a signal generator 224, an optional temperature sensor 226, and a storage medium 228. The electrical circuitry 216 may have other configurations including those with additional components.

The signal generator 224 provides an electrical input signal to the sensor interface 218 in response to the processor 222. In optical systems, the electrical input signal may be used to operate or control the detector and light source in the sensor interface 218. In electrochemical systems, the electrical input signal may be transmitted by the sensor interface 218 to the sample interface 214 to apply the electrical input signal to the reservoir 208 and thus, to the sample.

The electrical input signal may be a potential or current and may be constant, variable, or a combination thereof, such as when an AC signal is applied with a DC signal offset. The electrical input signal may be applied as a single pulse or in multiple pulses, sequences, or cycles. The signal generator 224 also may record an output signal from the sensor interface 218 as a generator-recorder.

The storage medium 228 may be a magnetic, optical, or semiconductor memory, another computer readable storage device, or the like. The storage medium 228 may be a fixed memory device or a removable memory device such as a memory card.

The processor 222 may implement analyte analysis and data treatment using computer readable software code and data stored in the storage medium 228. The processor 222 may start the analyte analysis in response to the presence of the sensor strip 204 at the sensor interface 218, the application of a sample to the sensor strip 204, in response to user input, or the like. The processor 222 may direct the signal generator 224 to provide the electrical input signal to the sensor interface 218. The processor 222 may receive the sample temperature from the temperature sensor 226, if so equipped.

The processor 222 receives the output signal from the sensor interface 218. The output signal is generated in response to the redox reaction of the analyte in the sample. The output signal may be generated using an optical system, an electrochemical system, or the like. The processor 222 may determine the concentration of the analyte in the sample from one or more output signals using a correlation equation. The results of the analyte analysis are output to the display 220 and may be stored in the storage medium 228.

The correlation equations relating analyte concentrations and output signals may be represented graphically, mathematically, a combination thereof, or the like. The correlation equations may be represented by a program number assignment (PNA) table, another look-up table, or the like that is stored in the storage medium 228. Instructions regarding implementation of the analysis may be provided by the computer readable software code stored in the storage medium 228. The code may be object code or any other code describing or controlling the functionality described herein. The data from the analyte analysis may be subjected to one or more data treatments, including the determination of decay rates, K constants, slopes, intercepts, and/or sample temperature in the processor 222.

In electrochemical systems, the sensor interface 218 is in electrical or optical communication with the sample interface 214. Electrical communication includes the transfer of input and/or output signals between contacts in the sensor interface 218 and conductors in the sample interface 214. Electrical communication may be implemented wirelessly or through physical contact, for example. The sensor interface 218 transmits the electrical input signal from the signal generator 224 through the contacts to the connectors in the sample interface 214. The sensor interface 218 also transmits the output signal from the sample through the contacts to the processor 222 and/or the signal generator 224.

Optical communication includes the transfer of light between an optical portal in the sample interface 202 and a detector in the sensor interface 208. Optical communication also includes the transfer of light between an optical portal in the sample interface 202 and a light source in the sensor interface 208.

The display 220 may be analog or digital. The display 220 may be a LCD, LED, or vacuum fluorescent display adapted to displaying a numerical reading.

In use, a liquid sample for analysis is transferred into the reservoir 208 by introducing the liquid to the opening 212. The liquid sample flows through the channel 210 and into the reservoir 208, while expelling the previously contained air. The liquid sample chemically reacts with the reagents deposited in the channel 210 and/or the reservoir 208. The processor 222 directs the signal generator 224 to provide an input signal to the sensor interface 218. In an optical system, the sensor interface 218 operates the detector and light source in response to the input signal. In an electrochemical system, the sensor interface 218 provides the input signal to the sample through the sample interface 214. The processor 222 receives the output signal generated in response to the redox reaction of the analyte in the sample. The processor 222 determines the analyte concentration of the sample using one or more correlation equations. The determined analyte concentration may be displayed and/or stored for future reference.

Figure 3:
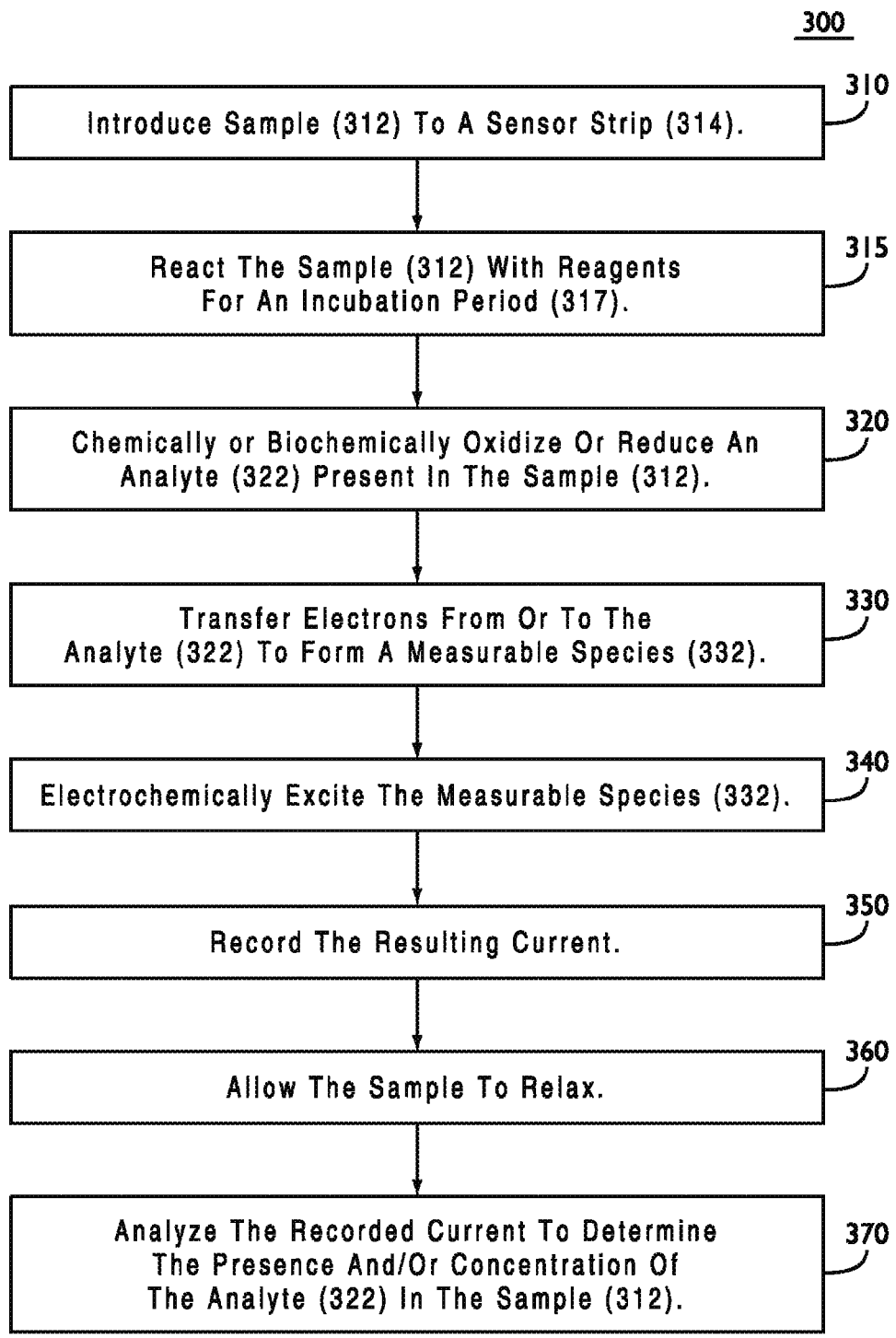
FIG. 3 represents a flowchart of an electrochemical method for determining the presence and/or concentration of an analyte in a sample.

FIG. 3 represents a flowchart of an electrochemical analysis 300 for determining the presence and optionally the concentration of an analyte 322 in a sample 312. In 310, the sample 312 is introduced to a sensor strip 314, such as the sensor strip depicted in FIGS. 1A-1B and 2A. The reagent layers, such as 275 and/or 285 depicted in FIG. 2A, begin to solubilize into the sample 312, thus allowing reaction.

In 315, an initial incubation period 317 allows the reagents to react with the sample 312 before an input signal is applied. Preferably, the incubation period 317 may be from 0.1 to 10 seconds, more preferably from 0.1 to 8 seconds or from 0.5 to 4 seconds. At present, from 0.1 to 1 second is more preferred for the incubation period 317. Other incubation periods may be used.

During the incubation period 317, a portion of the analyte 322 present in the sample 312 is chemically or biochemically oxidized or reduced in 320 by way of a redox reaction to form a measurable species 332. The measurable species 332 may be the oxidized or reduced analyte 322 or a mediator. Upon oxidation or reduction, electrons may be transferred to or from the analyte 322 and to or from measurable species 332 in 330. For example, a mediator may be reduced to form the measurable species 332 through oxidation of the analyte 322. Preferably, the measurable species 332 formed during the incubation period 317 is not electrochemically excited during the incubation period 317.

In 340, the measurable species 332 is electrochemically excited (oxidized or reduced). In this manner, electrons are selectively transferred between the analyte 322 and the working electrode of the sensor strip 314. The excitation 340 may be from 0.1 to 5 seconds or from 0.1 to 1 second in duration. The excitation 340 may be repeated.

In 350, the current produced during the excitation 340 may be recorded as a function of time. If multiple excitations 340 are applied to the sensor strip 314, one or more of the currents resulting from the excitations 340 may be recorded in 350. The currents may be recorded by a measurement device.

In 360, the sample undergoes relaxation. Preferably, current is not recorded during the relaxation 360. The relaxation 360 may follow each of the excitations 340 when multiple excitations are applied. During the relaxation 360, the current present during the excitation 340 is substantially reduced by at least one-half, preferably by an order of magnitude, and more preferably to zero. Preferably, a zero current state is provided by an open circuit or other method known to those of ordinary skill in the art to provide a substantially zero current flow. The measurement device may open the circuit through the sensor strip 314 to provide the open circuit. If a zero current state is provided, the relaxation 360 may be considered an intermittent incubation period.

The relaxation 360 may be at least 0.1 or at least 0.5 seconds in duration. The relaxation 360 may be from 0.1 to 3 seconds, from 0.2 to 2 seconds, or from 0.5 to 1 second in duration. Other relaxation durations may be used.

In 370, one or more of the recorded current and time values from 350 may be analyzed to determine the presence and/or concentration of the analyte 322 in the sample 312. Preferably, the analyte concentration is determined from a current measurement taken within 2 seconds or 1 second of the start of the initially applied excitation. More preferably, multiple short excitations are combined with a current measurement taken within 2 seconds, 1 second, or less from the start of the initially applied input signal to determine the analyte concentration of the sample. The recorded current and time values may be correlated to the concentration of the analyte 322 in the sample 312 using one or more correlation equations.

The excitation 340 and the relaxation 360 constitute a single duty cycle. Preferably, the input signal applied to the sensor strip 314 includes at least 2, 4, or 6 duty cycles applied within an independently selected 3, 5, 7, or 9 second time period. Thus, from the initial application of the input signal, the total time required for the excitation 340 and the relaxation 360 portions of the electrochemical analysis 300 may be at most 3, at most 5, at most 7, or at most 9 seconds. The duty cycles may be applied during a 1 to 3 second time period. From 2 to 6 duty cycles may be applied within 8 seconds or less. From 2 to 4 duty cycles may be applied within 3 to 6 seconds. Other time periods may be used.

For continuous monitoring, as may be used with implanted or partially implanted sensors, the duty cycles may be continuously repeated. The energy required to operate the system may be reduced and the service life of the system may be extended in relation to methods lacking relaxations. Furthermore, the application of multiple duty cycles may be separated by longer time periods, such as 5 minutes or more.

Amperometric sensor systems apply a potential (voltage) to the electrodes to excite the measurable species while the current (amperage) is monitored. Conventional amperometric sensor systems may maintain the excitation potential while continuously measuring the current for from 5 to 10 seconds, for example. In contrast to conventional methods, the input signals used in the electrochemical analysis 300 may replace continuous, long-duration excitations with multiple excitations and relaxations of relatively short duration. A more detailed description of multiple excitation and relaxation or "gated" pulse sequences applied as input signals may be found in WO 2007/013915, filed Jul. 19, 2006, entitled "Gated Amperometry."

When the short initial incubation times and/or gated input signals of the present invention are used, transient or non-Cottrell current decays may result. Not relying on a −0.5 Cottrell decay constant to determine the concentration of the analyte 322 in the sample 312 allows for completion of the electrochemical analysis 300 using transient decays within 8 seconds or less, within 4 seconds or less, or more preferably, within 3 seconds or less. The electrochemical analysis 300 may be completed in 2 seconds or less. The electrochemical analysis 300 may be completed in from about 0.5 to about 3 seconds. The electrochemical analysis 300 using transient decays may be complete using other time periods.

Figure 4A:
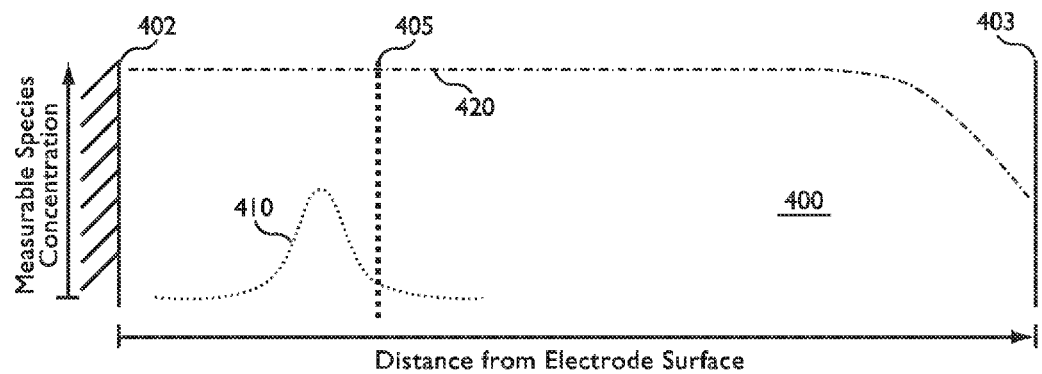
FIG. 4A represents a sample reservoir bounded by a lower electrode surface and an upper lid.

FIG. 4A represents a sample reservoir 400 bounded by a lower electrode surface 402 and an upper lid 403. A virtual upper boundary 405 of the reagent layer also is represented. Thus, the area between the electrode surface 402 and the virtual upper boundary 405 represents the sample contained by the reagent layer. Similarly, the area between the virtual upper boundary 405 and the upper lid 403 represents the sample above the reagent layer. The x-axis represents distance from the electrode surface, while the y-axis represents the sample concentration of measurable species generated from the redox reaction of the analyte. The figure omits the effect of analyte partitioning between a DBL and the liquid sample within the remaining portion of the reservoir 400.

Concentration profile 410 represents what would be observed immediately after introducing the sample to a strip, while concentration profile 420 represents what would be observed after a relatively long incubation period. The concentration profile 410 represents a transient condition, while the concentration profile 420 represents a Cottrell condition. Multiple transient states may exist between the transient concentration profile 410 and the Cottrell concentration profile 420.

Figure 4B:
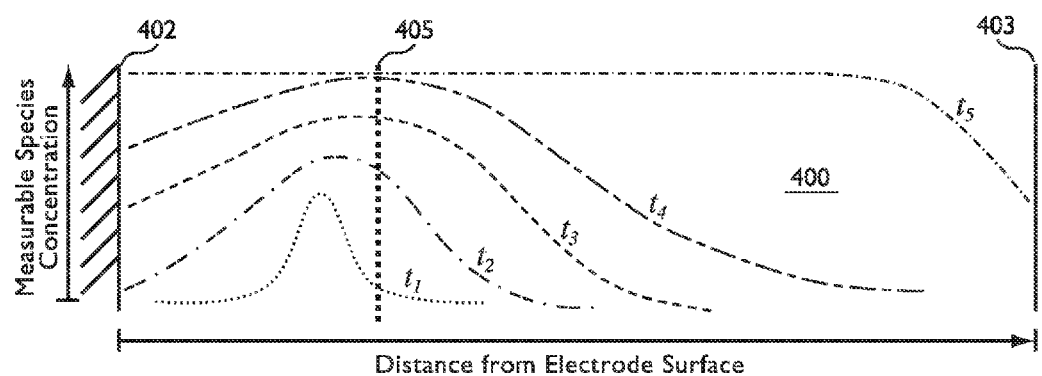
FIG. 4B represents concentration profiles formed from the sensor system when incubation times $t_1$ through $t_5$ pass before application of an input signal.

FIG. 4B represents the formation of different concentration profiles when incubation times $t_1$ through $t_5$ pass before the input signal is applied to the electrodes. The concentration profile at $t_5$, representing a 15 to 30 second incubation period, depicts a substantially constant concentration distribution of measurable species throughout the sample, which would provide a Cottrell decay having a decay constant of −0.5. Thus, the area under the $t_5$ line and the related measurable species concentration does not substantially change until a relatively large distance away from the electrode surface 402.

In contrast to the $t_5$ line, the $t_4$ line has an incubation period of 1 to 12 seconds and a variant concentration distribution of measurable species in the sample. The $t_4$ line has slower transient decay constants from −0.30 (1 second) to −0.48 (12 seconds). Thus, the area under the $t_4$ line and the underlying measurable species concentration undergoes a substantial change from the electrode surface 402 to the upper lid 403 of the reservoir 400 thus being variant.

As the incubation period is further reduced to 0.4 to 1 second in $t_3$ or to 0.1 to 0.3 second in $t_2$, the transient decay constants may range from −0.25 to −0.3 for $t_3$ and from −0.15 to −0.25 for $t_2$, respectively. The $t_1$ decay, representing a 0.01 to 0.1 second incubation period may have a transient decay constant of −0.15 or less. As the incubation period is reduced from $t_4$ to $t_1$, the area under the lines and the related measurable species concentration between the electrode surface 402 and the upper lid 403 of the reservoir 400 becomes increasingly variant.

By having a lower concentration of the measurable species at the electrode surface 402 than in the remaining portion of the reservoir 400, such as represented by the $t_1$ through $t_4$ variant concentration distribution profiles of FIG. 4B, the rate of current decay may be slower than the −0.5 decay constant required for Cottrell decay. This slower decay may be attributable to the large concentration of measurable species farther from the electrode surface 402 reaching the electrode surface more rapidly than if the measurable species was distributed evenly throughout the sample reservoir 400. Similarly, faster decay rates may be obtained when a higher concentration of the measurable species is present at the electrode surface 402 than in the remaining portion of the sample reservoir 400.

Figure 4C:
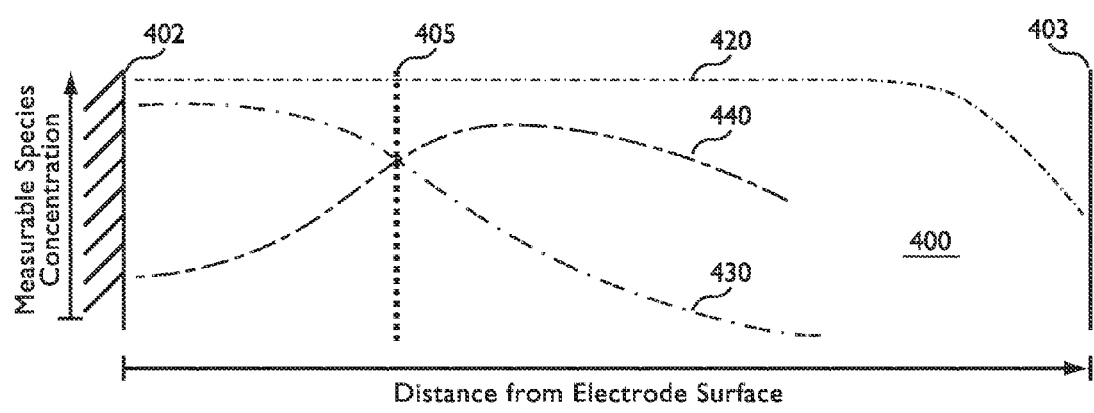
FIG. 4C represents the relation between measurable species concentrations in the reservoir and rates of current decay.

FIG. 4C represents the relation between measurable species concentrations in the reservoir 400 and current decay constants. Measurable species concentration profiles 430 and 440 have slower and faster decay rates, respectively, than 420, which corresponds to the −0.5 Cottrell decay constant. For concentration profile 430 having a decay constant less than the −0.5 Cottrell decay constant, such as −0.3, the rate of current decay will be slower than that observed for a Cottrell system. Similarly, for concentration profile 440 having a decay constant greater than the −0.5 Cottrell decay constant, such as −0.7, the rate of current decay will be faster than that observed for a Cottrell system. Thus, in comparison to the −0.5 Cottrell decay constant represented by 420, transient decay constants 430, 440 reflect variant concentration distributions of the measurable species in the reservoir 400.

When long incubation periods are used to generate Cottrell decay, the amount of measurable species produced during the measurement excitation is small compared to the amount of measurable species produced during the prior incubation period. Thus, unlike the concentration profile 420 representing complete redox conversion of the analyte to a measurable species before application of the input signal, concentration profiles 430, 440 represent incomplete conversion. Furthermore, any change in diffusion rate of the measurable species to the electrode from convection or other pathways also is small in relation to the amount of measurable species generated during the incubation period. Thus, long incubation periods substantially negate effects that would alter the −0.5 Cottrell decay constant.

In contrast, when short incubation periods, such as 12 seconds, 10 seconds, and shorter are used, the amount of measurable species produced during the measurement excitation and any change in diffusion rates from processes other than diffusion may provide an actual decay rate that is slower than the −0.5 Cottrell value. This decay process can be described by the following normalized current equation, Equation (2):

$$f(t) = t^{-a+b+c} \quad (2),$$

where a is the portion of the decay constant from measurable species formed during the incubation period, b is the portion of the decay constant from measurable species formed during the measurement excitation, and c is the portion of the decay constant arising from variations in the concentration distribution of the measurable species in the sample reservoir. Negative values of b and c result in an increase in measured measurable species concentration, while positive values of b and c result in a decrease in measured measurable species concentration. Thus, if either a or b are non-zero, a deviation from the a decay value will result. As a Cottrell decay is provided by a −0.5 value for a, a significant contribution from b or c provides a transient decay constant. Under Equation (2), term a controls the decay constant obtained from the concentration profile 420, while term b would significantly contribute to the decay constant obtained from the concentration profiles 430 and 440, where the input signal is applied before redox conversion of the analyte is complete.

Equation (2) establishes that the decay constant of a system can vary over time in response to which of these underlying factors affect the current decay at the time of measurement. For example, longer incubation periods increase a while reducing b because the more analyte converted to the measurable species during the incubation period, the less analyte remains in the sample for conversion to the measurable species during the excitation.

The redox conversion of analyte to measurable species occurs in hydrated reagent layers. Because thicker reagent layers require longer to hydrate, thicker reagent layers will provide an increase in the b term in relation to the a term if the input signal is applied before the reagent layer is hydrated. Cottrell decay is not observed before the reagent layer is hydrated due to the contribution to the decay constant of measurable species formed during the measurement excitation, the b term of Equation (2). This was recognized in column 4, lines 58-59 of the '069 patent, which discloses that incomplete wetting of the reagent results in a failure of the system to follow the Cottrell curve decay, resulting in an inaccurate analyte concentration value being obtained. Thus, transient decay constants may be obtained from partially hydrated reagent layers resulting from relatively short initial incubation periods.

Sensor strip reservoirs including a substantially constant concentration distribution of the measurable species may reduce any affect on the decay constant attributable to c. The c term also may affect the decay constant if the excitation duration is too long for the sample volume, resulting in a rapid decrease in the measurable species concentration as the distance increases from the surface of the electrode. Using a short excitation or multiple short excitations combined with one or multiple relaxations may assist in reducing the effect of the c term on the decay constant.

For example, the '069 patent describes a system that provides a −0.5 Cottrell decay constant when a 160 second initial incubation period is combined with a 50 μL sample reservoir. For this system, if the incubation period were sufficiently shortened, the b term of Equation (2) would increase, thus providing non-Cottrell decay. Similarly, if the reservoir volume were sufficiently reduced, non-Cottrell decay would result from an increase in the c term of Equation (2).

Figure 5:
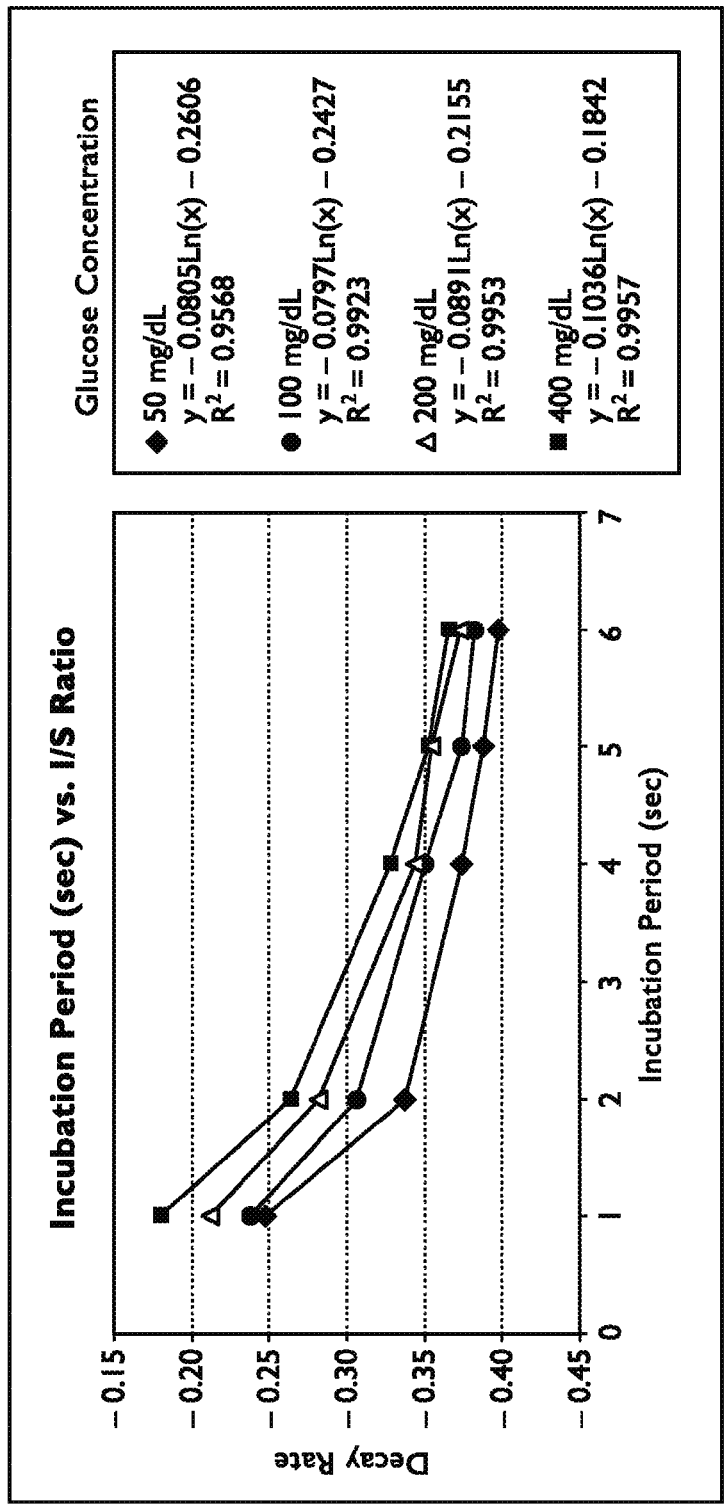
FIG. 5 depicts decay rates obtained from working electrodes after varying incubation periods for whole blood samples containing 50, 100, 200, or 400 mg/dL of glucose.

FIG. 5 depicts decay constants obtained from sensor strips having reservoir volumes of about 3.5 μL and electrode to lid distances of about 250 μm after varying incubation periods for whole blood samples containing 50, 100, 200, or 400 mg/dl of glucose. The rate of decay increased with increasing incubation time; however, a Cottrell decay constant of −0.5 was not obtained within the six second incubation period. Thus, the system provided transient decays under these circumstances.

Table I, below, provides the decay constants for the 1-6 second incubation periods of FIG. 5 and provides projected constants for 10 and 15 second incubation periods. A projected decay constant also is provided for an extended 20 second incubation period.

TABLE I

| Input Signal | Incubation Period | 50 mg/dL | 100 mg/dL | 200 mg/dL | 400 mg/dL |
|---|---|---|---|---|---|
| 4-1-1 | 1 | −0.2479 | −0.23823 | −0.2119 | −0.17947 |
| 4-2-1 | 2 | −0.337 | −0.30593 | −0.282 | −0.2631 |
| 4-4-1 | 4 | −0.37417 | −0.34993 | −0.3442 | −0.32837 |
| 4-5-1 | 5 | −0.3877 | −0.3734 | −0.3549 | −0.35283 |
| 4-6-1 | 6 | −0.3979 | −0.38273 | −0.373 | −0.36483 |
| Projected | 10 | −0.44596 | −0.42622 | −0.42066 | −0.42275 |
| Projected | 15 | −0.4786 | −0.45853 | −0.45679 | −0.46475 |
| Projected | 20 | −0.50176 | −0.48146 | −0.48242 | −0.49456 |

In each instance, the input signal included an initial excitation of four seconds, followed by an open circuit type intermittent incubation period of varying duration, and a measurement excitation of one second during which the current was recorded. The sensor system did not achieve Cottrell decay condition during any of the incubation periods from one to six seconds. The sensor system would not be projected to achieve a Cottrell decay condition within twelve seconds even at low 50 mg/dl glucose concentrations. Preferable transient decay constants are from −0.001 to −0.48 and from −0.52 to −1. More preferable transient decay constants are at most −0.45, at most 0.35, and at most −0.3. Other transient decay constants may be used.

Figure 6A:
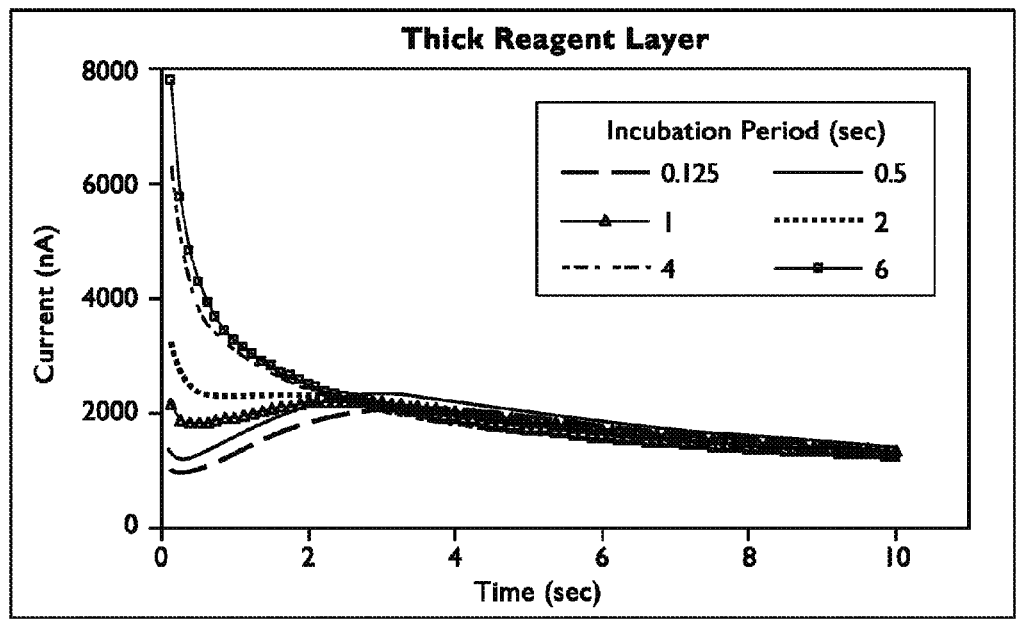
FIGS. 6A-6C plot the current profiles obtained from three sensor strips each having a different average initial thickness of the reaction layer at multiple initial incubation periods.
Figure 6B:
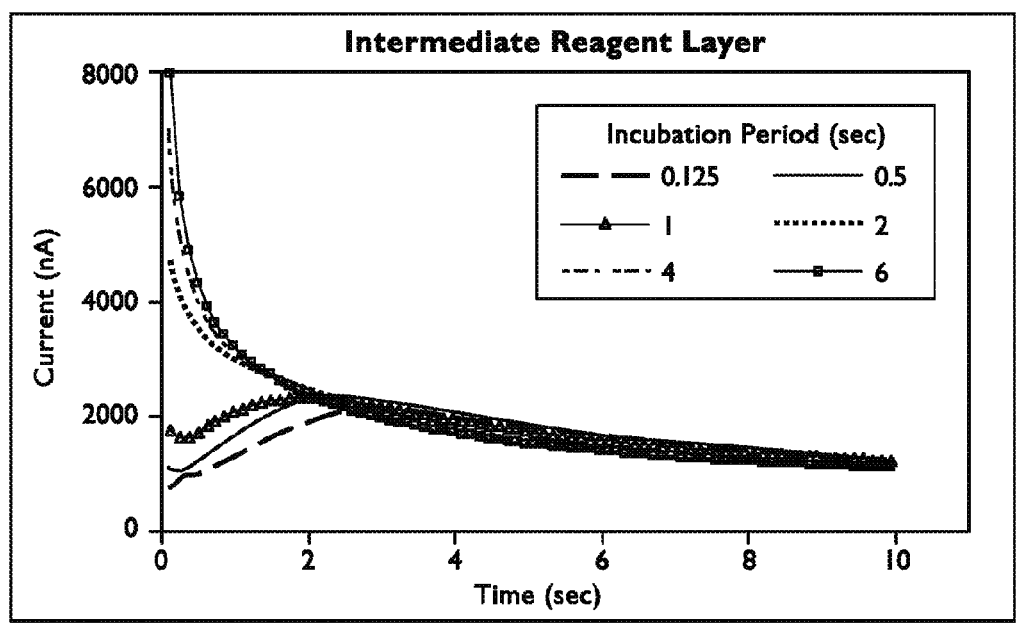
Figure 6C:
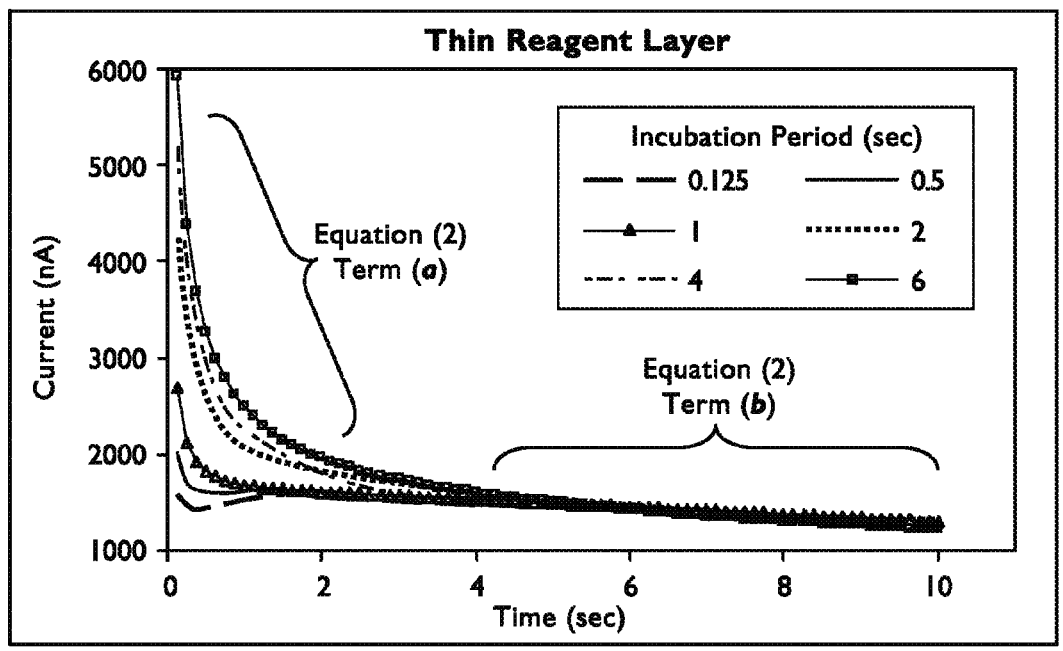

FIGS. 6A-6C plot the current profiles obtained from three sensor strips each having a different average initial thickness of the reaction layer at initial incubation periods of 0.125, 0.5, 1, 2, 4, and 6 seconds. The sample reservoir of each strip was about 1 μL. The FIG. 6A plot was obtained from multiple sensor strips having reaction layers with an average initial thickness from about 15 μm to about 20 μm ("thick"). The FIGS. 6B and 6C plots were obtained from multiple sensor strips having reaction layers with average initial thicknesses from 10 μm to 15 μm ("intermediate") and from 1 μm to 2 μm ("thin"), respectively. Other thicknesses may be used.

The figures establish the relationship of incubation time, reagent layer thickness, and the associated rate of layer hydration. Thicker reagent layers required a longer time for the reagent layer to hydrate, and the greater the time required for the reagent layer to hydrate, the longer the time before the current decay reached a point of continual decrease. Current values obtained from decreasing transient decays are preferred for correlating with the analyte concentration of the sample.

For the thick layered strips of FIG. 6A, continually decreasing current decays were obtained after an incubation period of about 4 seconds or greater. However, for incubation periods of about 2 seconds and less, a continually decreasing current decay was not obtained for thick layered strips until about 2 or more seconds of input signal were applied.

For the intermediate thickness reagent layer of the FIG. 6B sensor strips, continually decreasing current decays were obtained after an incubation period of about 2 seconds or greater. For incubation periods of about 1 second and less, about 2 or more seconds of input signal provided a continually decreasing current decay.

For the thin reagent layer of the FIG. 6C sensor strips, continually decreasing current decays were obtained after an incubation period of about 1 second or greater. For incubation periods of about 0.5 second and less, about 1 or more seconds of input signal provided a continually decreasing current decay. Thus, thinner reagent layers may be combined with shorter incubation periods to provide a shorter total analysis time, while thicker reagent layers may require longer duration incubation periods and/or input signals.

Figure 7A:
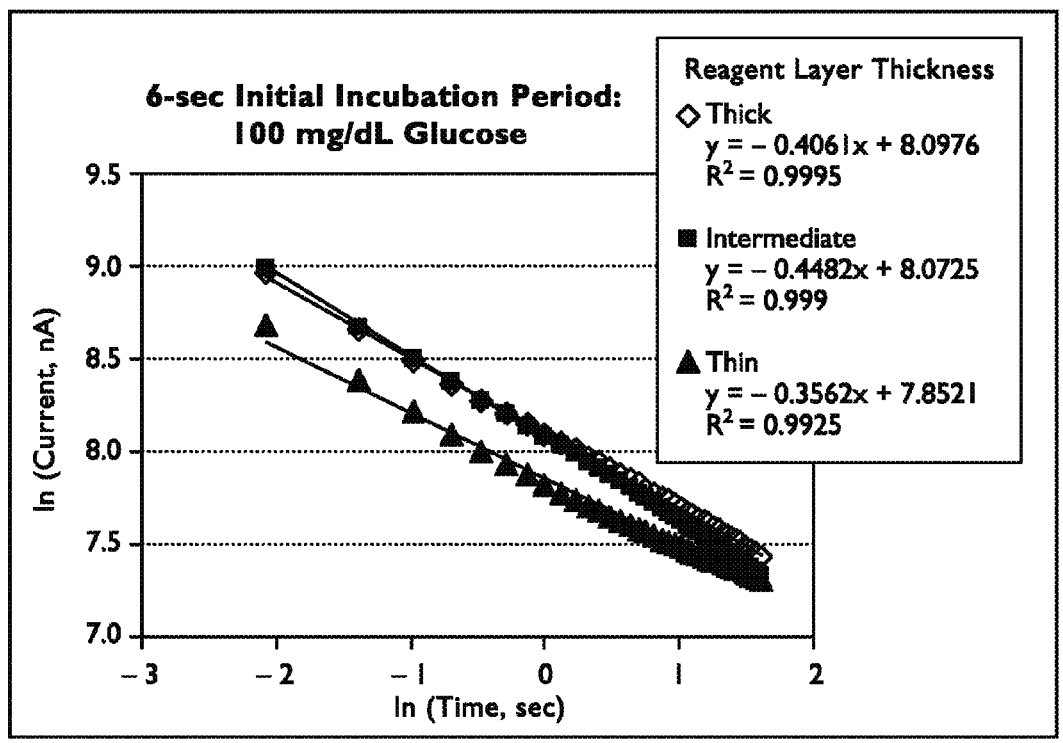
FIGS. 7A-7B plot the natural logs of current vs. time for whole blood samples including 100 or 300 mg/dL of glucose at 40% hematocrit obtained after a 6 second initial incubation period.
Figure 7B:
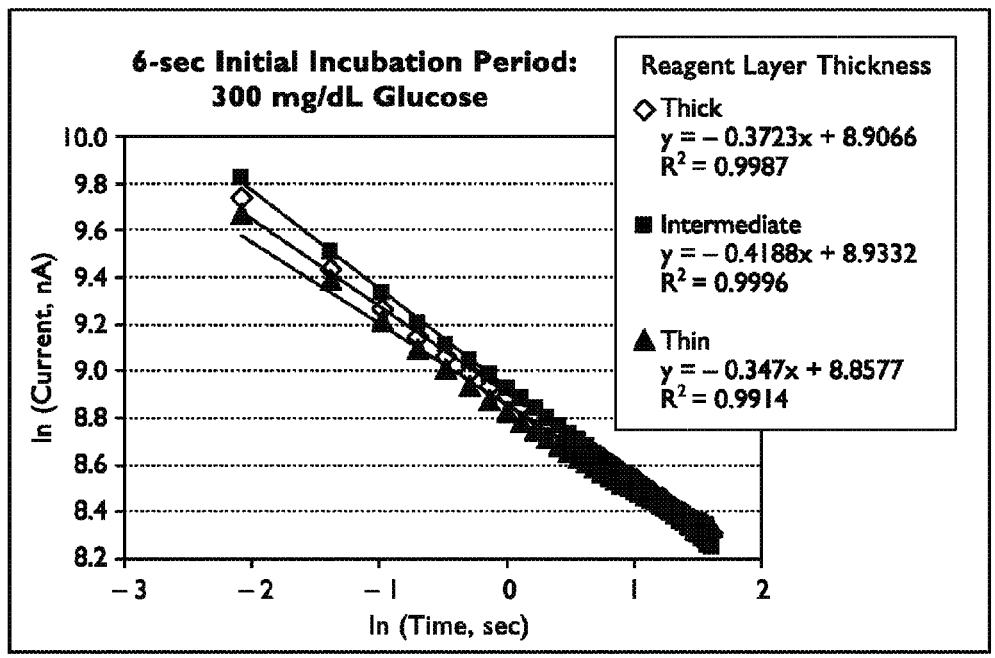

FIGS. 7A-7B plot the natural logs of current vs. time for whole blood samples including 100 or 300 mg/dL of glucose at 40% hematocrit obtained after a 6 second initial incubation period. The sample reservoir volumes and reagent layer initial average thicknesses were as in FIGS. 6A-6C, above. The plots were generated from current values obtained during the first 5 seconds of a 10 second excitation, where the a term of Equation (2) dominates the decay constant. Each of the observed decay constants—slopes of the ln(current, nA) vs. ln(time, sec) plots—differ from the −0.5 Cottrell decay constant, having transient decay constants ranging from about −0.35 to about −0.45. Thus, even at the longest initial incubation period of 6 seconds, Cottrell decay is not observed.

Figure 8A:
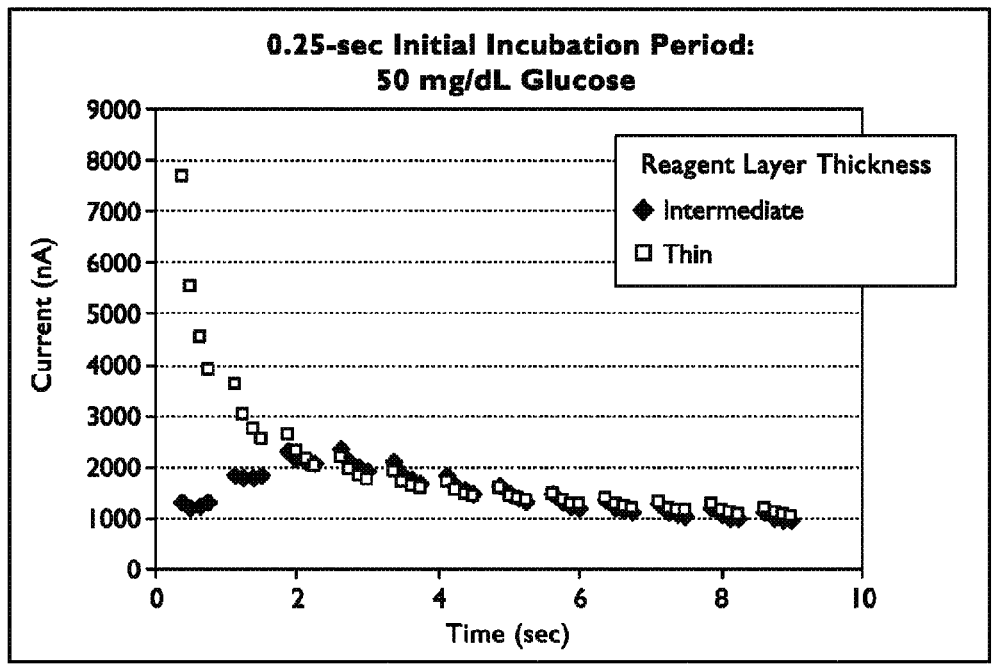
FIGS. 8A-8C are current decay profiles from a 0.25 second incubation period followed by a gated input signal having excitation times of 0.5 second and relaxation times of 0.25 second.
Figure 8B:
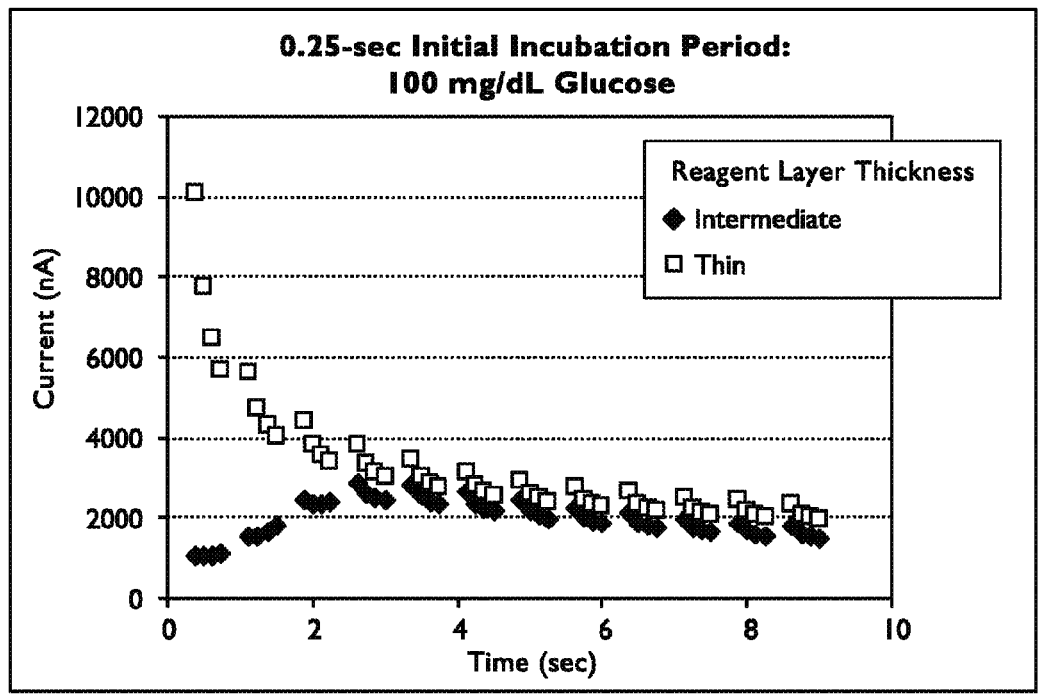
Figure 8C:
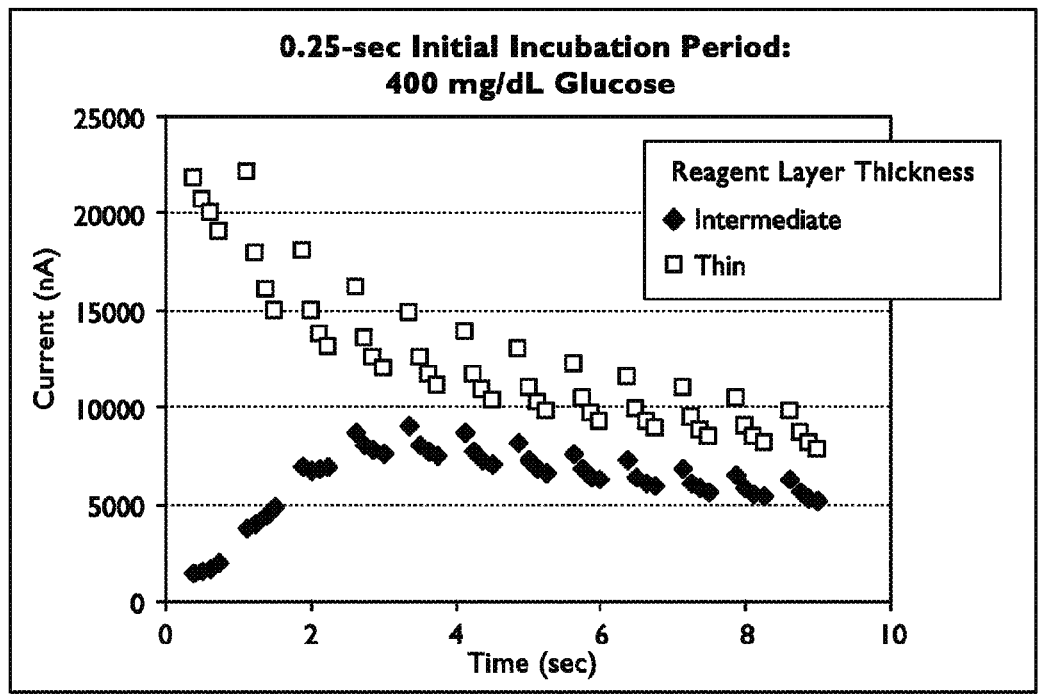

FIGS. 8A-8C are current decay profiles from a 0.25 second initial incubation period followed by a gated input signal including 0.5 second excitations and 0.25 second relaxations, to provide a duty cycle duration of 0.75 second. Both intermediate and thin reagent layer sensor strips having sample reservoir volumes of about 1 μL were used to analyze whole blood samples including 50, 100, or 400 mg/dL of glucose at 40% hematocrit. Continually decreasing current decays that may be correlated to the 50 mg/dL analyte concentration in the sample were obtained within 0.75 second for the thin reagent layer, thus during the first excitation. For the thicker intermediate reagent layer, continually decreasing current decays were obtained within 3 seconds, thus during the third excitation.

Figure 8D:
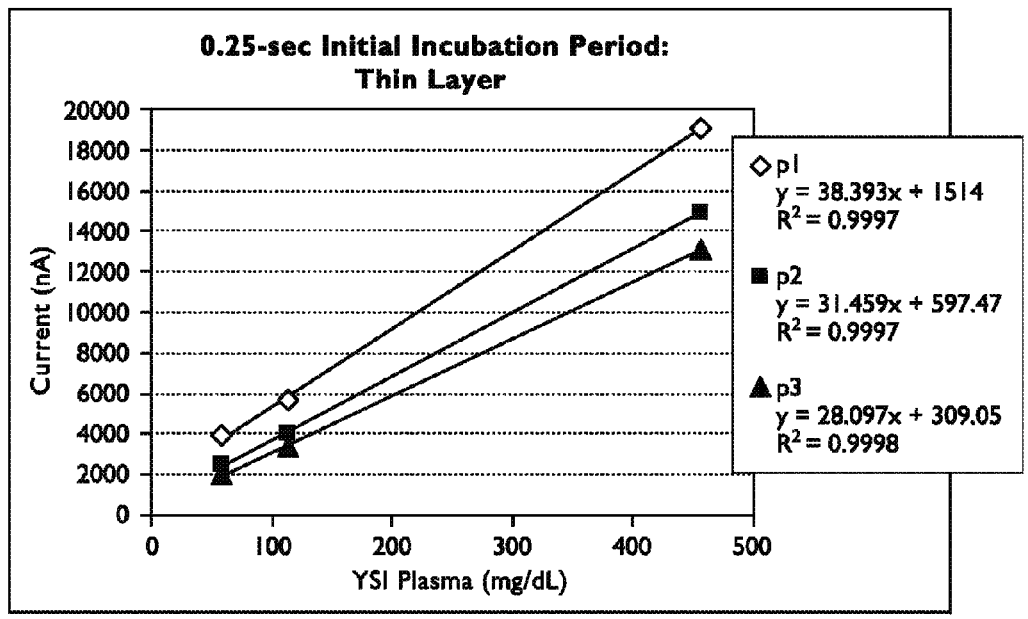
FIG. 8D is a calibration plot obtained by plotting the end-point currents (p1, p2, p3) of the first three excitations obtained from thin reagent layer sensor strips as depicted in FIGS. 8A-8C.

FIG. 8D is a calibration plot obtained by plotting the endpoint currents (p1, p2, p3) of the first three excitations obtained from thin reagent layer sensor strips as depicted in FIGS. 8A-8C. The figure establishes that current values taken after very short incubation periods of 0.25 second in accord with the present invention may be accurately correlated ($R^2=0.999$) with the actual plasma glucose concentration of whole blood samples.

Figure 8E:
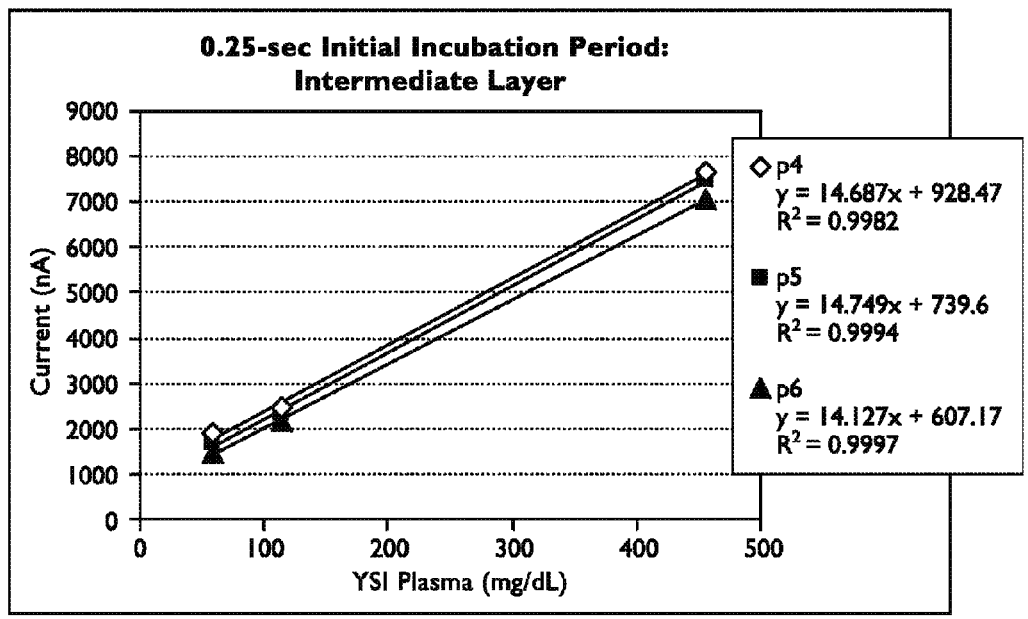
FIG. 8E is a calibration plot obtained by plotting the end-point currents (p4, p5, p6) of excitations 4, 5, and 6 obtained from sensor strips having intermediate thickness reagent layers as depicted in FIGS. 8A-8C.

FIG. 8E is a calibration plot obtained by plotting the endpoint currents (p4, p5, p6) of excitations 4, 5, and 6 obtained from sensor strips having intermediate thickness reagent layers as depicted in FIGS. 8A-8C. The figure establishes that current values taken after a very short 0.25 second initial incubation period and multiple duty cycles including 0.5 second excitations and 0.25 second relaxations in accord with the present invention may be accurately correlated ($R^2=0.99$) with the actual plasma glucose concentration of whole blood samples.

To provide a clear and consistent understanding of the specification and claims of this application, the following definitions are provided.

"Sample" is a composition that may contain an unknown amount of the analyte. A sample may be aqueous, such as whole blood, urine, saliva, or a derivative, such as an extract, a dilution, a filtrate, or a reconstituted precipitate.

"Incubation period" is the length of time that the sample reacts with the reagents before an excitation is applied, such as before the first excitation is applied and/or the time between excitations if the input signal includes multiple excitations.

"Measurable species" is any electrochemically active species that may be oxidized or reduced under an appropriate potential at an electrode surface.

An "Oxidoreductase" facilitates the oxidation or reduction of an analyte or biological substrate. See, for example the Oxford Dictionary of Biochemistry and Molecular Biology, Revised Edition, A. D. Smith, Ed., New York: Oxford University Press (1997) pp. 161, 476, 477, and 560.

While various embodiments of the invention have been described, it will be apparent to those of ordinary skill in the art that other embodiments and implementations are possible within the scope of the invention.

The invention claimed is:

1. A method for determining an analyte concentration in a sample, comprising:
    reacting an analyte in a sample with an ionizing agent;
    forming a measurable species from the reaction between the sample and the ionizing agent during an incubation period from 0.1 to 8 seconds, where the measurable species concentration in the sample is responsive to an analyte concentration in the sample;
    applying an input signal to the sample after the incubation period, where the input signal includes excitations and relaxations, where
        at least two of the excitations have a duration from 0.1 to 5 seconds, and where
        at least one of the relaxations has a duration from 0.4 to 1 second;
    generating an output signal from the excitation following the at least one of the relaxations having the duration from 0.4 to 1 second, the output signal having a transient decay responsive to a redox reaction of the measurable species; and
    determining the analyte concentration of the sample from the transient decay of the generated output signal.

2. The method of claim 1, where the output signal from which the analyte concentration of the sample is determined results from an excitation having a duration from 0.1 to 1 second.

3. The method of claim 1, the input signal including at least 4 excitations.

4. The method of claim 1, where
    the input signal includes at least 2 duty cycles applied within a 1 to 3 second time period of reacting the analyte in the sample with the ionizing agent, and where
    each of the at least 2 duty cycles includes an excitation and a relaxation.

5. The method of claim 1, where the relaxation having the duration from 0.4 to 1 second precedes the excitation generating the transient decay from which the analyte concentration of the sample is determined.

6. The method of claim 1, where the excitations are separated by at least two relaxations, each of the at least two relaxations having a duration from 0.1 to 3 seconds.

7. The method of claim 1, where the transient decay is attained within 0.5 to 5 seconds of applying the input signal to the sample.

8. The method of claim 1, where the transient decay is attained within about 0.5 to about 3 seconds of applying the input signal to the sample.

9. The method of claim 1, where the incubation period, the application of the input signal to the sample, and the determining the analyte concentration of the sample from the transient decay of the generated output signal are complete in at most 6 seconds.

10. The method of claim 1, where the incubation period, the application of the input signal to the sample, and the determining the analyte concentration of the sample from the transient decay of the generated output signal are complete in at most 4 seconds.

11. The method of claim 1, where the determining the analyte concentration of the sample from the transient decay of the generated output signal is complete within 3 seconds of applying the input signal to the sample.

12. The method of claim 1, where the generated output signal from which the analyte concentration is determined comprises a current value generated within 6 seconds of applying the input signal to the sample.

13. The method of claim 1, where the generated output signal from which the analyte concentration is determined comprises a current value generated within 2 seconds of applying the input signal to the sample.

14. The method of claim 1, where the applying the input signal to the sample is complete in at most 4 seconds.

15. The method of claim 1, where the transient decay has a decay constant from $-0.001$ to $-0.48$.

16. The method of claim 1, where the transient decay has a decay constant from $-0.52$ to $-1$.

17. The method of claim 1, where the transient decay has a decay constant of at most $-0.45$.

18. The method of claim 1, where the transient decay has a decay constant of at most $-0.35$.

19. The method of claim 1, where the measurable species comprises at least one mediator.

20. The method of claim 1, where the analyte is glucose and the sample is whole blood.

21. The method of claim 1, further comprising measuring decreasing currents from the transient decay.

22. The method of claim 21, where the determining the analyte concentration of the sample is from a current measurement, the current measurement determined from the decreasing currents of the transient decay.

23. The method of claim 22, where the current measurement is from a single excitation of the input signal.

24. The method of claim 23, where the current measurement is a single current value.

25. The method of claim 1, the sample residing in a reservoir defined by a sensor strip base and the bottom surface of a lid, where
the base is 20 to 250 micrometers from the bottom surface of the lid, and where
the volume of the sample within the reservoir is from 0.25 to 10 microliters.

26. The method of claim 25, further comprising generating a variant concentration distribution of the measurable species in the reservoir.

27. The method of claim 25, where
the volume of the sample within the reservoir is at most 3 microliters, and
the reservoir includes at least one reagent layer having an average initial thickness of at most 20 micrometers.

28. The method of claim 25, where the volume of the sample within the reservoir is from 0.5 to 1.5 microliter.

29. The method of claim 27, the at least one reagent layer having an average initial thickness of at most 10 micrometers.

30. The method of claim 25, where the reservoir includes at least one reagent layer having an average initial thickness of at most 2 micrometers when the input signal includes at least two excitations, and at least one of the excitations has a duration of at most 0.5 second.

31. The method of claim 25, where the base is at most 150 micrometers from the bottom surface of the lid, the volume of the sample within the reservoir is at most 3.5 microliters, the reservoir includes at least one reagent layer having an average initial thickness of at most 10 micrometers, and the incubation period is at most 6 seconds.

32. The method of claim 25, where the base is at most 100 micrometers from the bottom surface of the lid, the volume of the sample within the reservoir is at most 3 microliters, the reservoir includes at least one reagent layer having an average initial thickness of at most 2 micrometers, and the incubation period is at most 2 seconds.

33. A method for determining an analyte concentration in a sample, comprising:
reacting an analyte in a sample with an ionizing agent;
forming a measurable species from the reaction between the sample and the ionizing agent during an incubation period of at most 8 seconds, where the measurable species concentration in the sample is responsive to an analyte concentration in the sample;
applying an input signal to the sample after the incubation period, where
the input signal includes excitations and relaxations, where at least one of the excitations has a duration from 0.1 to 1 second, and where
at least one of the relaxations has a duration from 0.1 to 3 seconds;
generating an output signal from the at least one of the excitations having the duration from 0.1 to 1 second, the output signal having a transient decay responsive to a redox reaction of the measurable species; and
determining the analyte concentration of the sample from the transient decay of the generated output signal.

34. A method for determining an analyte concentration in a sample, comprising:
reacting an analyte in a sample with an ionizing agent;
forming a measurable species from a redox reaction between a portion of the analyte in the sample and the ionizing agent during an incubation period from 0.1 to 8 seconds;
applying an input signal to the sample after the incubation period;
generating an output signal responsive to the analyte concentration in the sample from the input signal, the output signal having a transient decay responsive to the measurable species formed from the portion of the analyte in the sample; and
determining the analyte concentration of the sample from the transient decay of the output signal within 3 seconds of applying the input signal to the sample.

35. A method for determining an analyte concentration in a sample, comprising:

reacting an analyte in a sample with an ionizing agent;

forming a measurable species from a redox reaction between the analyte in the sample and the ionizing agent during an incubation period of from 0.1 to 8 seconds;

applying an input signal to the sample after the incubation period, the input signal including excitations and relaxations, where at least two of the excitations have a duration from 0.1 to 5 seconds and at least two of the relaxations have a duration from 0.1 to 3 seconds;

generating an output signal responsive to the analyte concentration in the sample from at least one of the excitations within 0.5 to 5 seconds of reacting the analyte in the sample with the ionizing agent, the output signal having a transient decay of continually decreasing currents responsive to the measurable species; and determining the analyte concentration of the sample from the continually decreasing current decay of the output signal.

36. The method of claim 33, where the determining includes relating the output signal to the analyte concentration of the sample with a correlation equation.

37. The method of claim 33, where the determining the analyte concentration of the sample from the transient decay of the generated output signal includes determining the analyte concentration of the sample from a current measurement, the current measurement determined from the transient decay of the generated output signal.

38. The method of claim 35, where the determining includes relating the output signal to the analyte concentration of the sample with a correlation equation.

39. The method of claim 35, further comprising measuring the continually decreasing current decay is attained within about 0.5 to about 3 seconds of reacting the analyte in the sample with the ionizing agent.

40. The method of claim 1, where a first relaxation follows a first excitation, a second relaxation follows a second excitation, and a third excitation follows the second relaxation.

41. The method of claim 1, further comprising measuring currents from the transient decay and determining the analyte concentration of the sample from the measured currents.

42. The method of claim 1, the sample residing in a reservoir defined by a sensor strip, the reservoir including the ionizing agent, a working electrode, and a counter electrode, where the input signal applied to the sample passes through the working and the counter electrodes.

43. The method of claim 1, further comprising measuring the generated output signal and determining the analyte concentration of the sample from the transient decay of the measured output signal.

44. The method of claim 43, where the transient decay is measured within 0.5 to 5 seconds of applying the input signal to the sample.

45. The method of claim 43, where the transient decay is measured within about 0.5 to about 3 seconds of applying the input signal to the sample.

46. The method of claim 43, where the incubation period, the application of the input signal to the sample, and the determining the analyte concentration of the sample from the transient decay of the measured output signal are complete in at most 6 seconds.

47. The method of claim 43, where the incubation period, the application of the input signal to the sample, and the determining the analyte concentration of the sample from the transient decay of the measured output signal are complete in at most 4 seconds.

48. The method of claim 43, where the determining the analyte concentration of the sample from the transient decay of the measured output signal is complete within 3 seconds of applying the input signal to the sample.

49. The method of claim 43, where the generated output signal from which the analyte concentration is determined comprises a current value measured within 6 seconds of applying the input signal to the sample.

50. The method of claim 43, where the generated output signal from which the analyte concentration is determined comprises a current value measured within 2 seconds of applying the input signal to the sample.

* * * * *